United States Patent
Kofidis

(10) Patent No.: US 11,576,771 B2
(45) Date of Patent: Feb. 14, 2023

(54) METHOD FOR MANUFACTURING PERSONALIZED NATURALLY DESIGNED MITRAL PROSTHESIS

(71) Applicants: NATIONAL UNIVERSITY OF SINGAPORE, Singapore (SG); NATIONAL UNIVERSITY HOSPITAL (SINGAPORE) PTE LTD, Singapore (SG)

(72) Inventor: Theodoros Kofidis, Singapore (SG)

(73) Assignees: NATIONAL UNIVERSITY OF SINGAPORE, Singapore (SG); NATIONAL UNIVERSITY HOSPITAL (SINGAPORE) PTE LTD, Singapore (SG)

( * ) Notice: Subject to any disclaimer, the term of this patent is extended or adjusted under 35 U.S.C. 154(b) by 276 days.

(21) Appl. No.: 16/848,866

(22) Filed: Apr. 15, 2020

(65) Prior Publication Data
US 2020/0237514 A1    Jul. 30, 2020

Related U.S. Application Data

(63) Continuation-in-part of application No. 16/384,957, filed on Apr. 16, 2019, now Pat. No. 11,324,592, which is a continuation-in-part of application No. 15/766,377, filed as application No.
(Continued)

(51) Int. Cl.
*A61F 2/24* (2006.01)
*A61B 34/10* (2016.01)
*G06T 7/00* (2017.01)

(52) U.S. Cl.
CPC ............ *A61F 2/2415* (2013.01); *A61B 34/10* (2016.02); *A61F 2/2409* (2013.01); *A61F 2/2412* (2013.01); *A61F 2/2457* (2013.01); *G06T 7/0012* (2013.01); *A61B 2034/102* (2016.02); *A61B 2034/104* (2016.02); *A61B 2034/105* (2016.02); *A61B 2034/108* (2016.02); *A61F 2/2469* (2013.01); *A61F 2/2496* (2013.01); *A61F 2220/0075* (2013.01); *A61F 2240/002* (2013.01)

(58) Field of Classification Search
CPC .............. A61B 34/10; A61B 2034/102; A61B 2034/104; A61B 2034/105; A61B 2034/108; A61F 2/2409; A61F 2/2412; A61F 2/2415; A61F 2/2457; G06T 7/0012
See application file for complete search history.

(56) References Cited

U.S. PATENT DOCUMENTS

| | | | |
|---|---|---|---|
| 6,358,277 B1 * | 3/2002 | Duran | A61F 2/2496 623/23.72 |
| 2014/0088698 A1 * | 3/2014 | Roels | A61F 2/2409 623/2.38 |
| 2017/0057169 A1 * | 3/2017 | Grbic | A61F 2/2415 |

* cited by examiner

*Primary Examiner* — Suba Ganesan
(74) *Attorney, Agent, or Firm* — Soroker Agmon Nordman PTE LTD

(57) ABSTRACT

A method for manufacturing a personalized naturally designed mitral valve prosthesis to precisely fit a specific patient for which the valve prosthesis is made for is provided. The method includes measuring size and shape of a mitral valve of the specific patient by using imaging methods, calculating geometry and dimensions of annular ring, leaflets and chords per the specific patient based on validated algorithms, and cutting and connecting the annular ring, leaflets and chords to form a personalized prosthesis mitral valve.

36 Claims, 21 Drawing Sheets

Related U.S. Application Data

PCT/SG2016/050498 on Oct. 10, 2016, now Pat. No. 10,709,560.

(60) Provisional application No. 62/239,036, filed on Oct. 8, 2015.

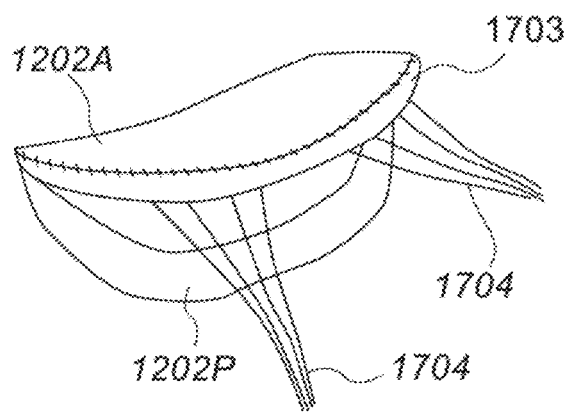
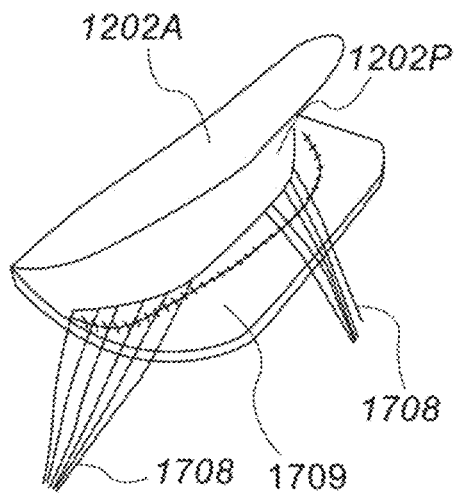
FIG. 15A    FIG. 15B
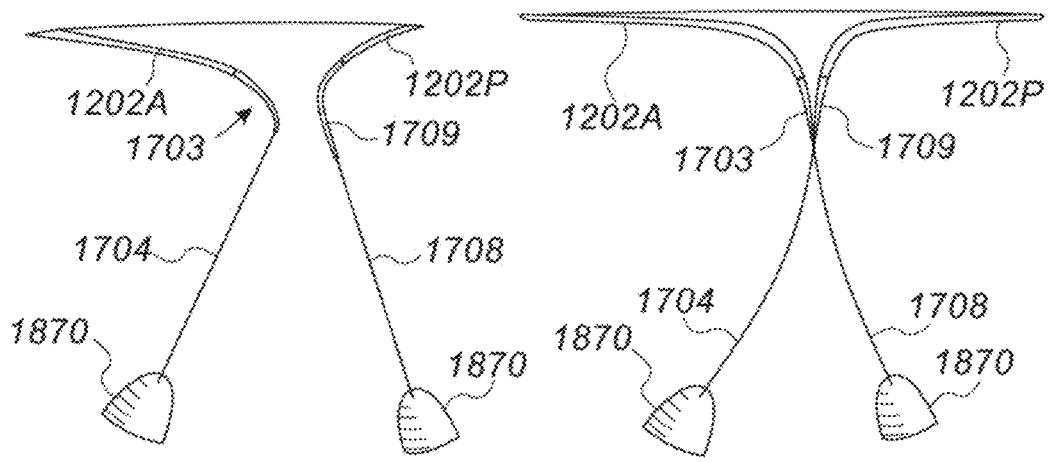
FIG. 16A    FIG. 16B

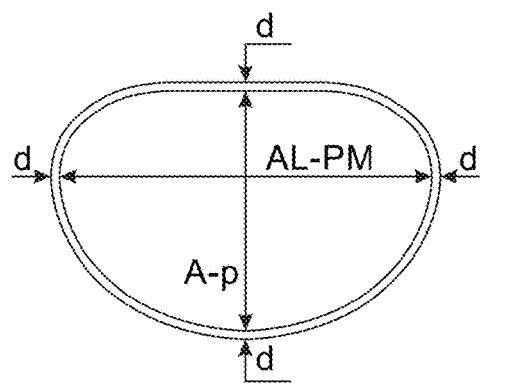
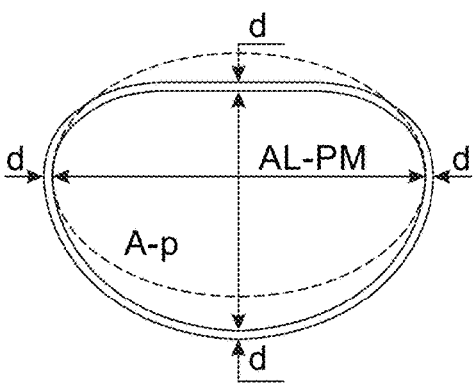
FIG. 21A    FIG. 21B
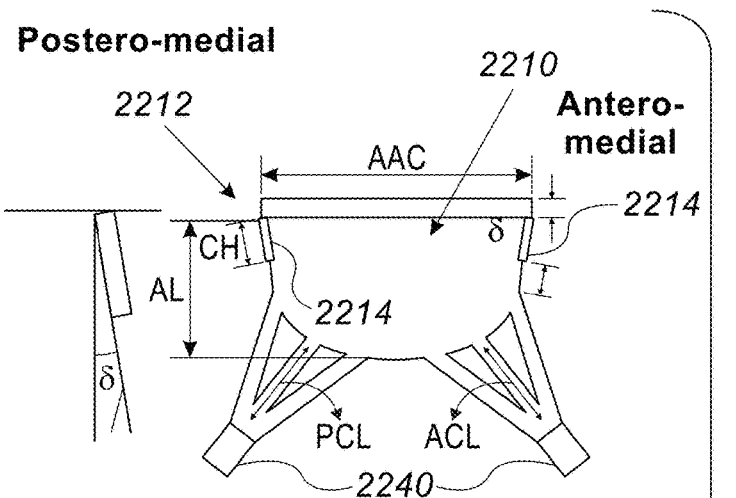
FIG. 22A
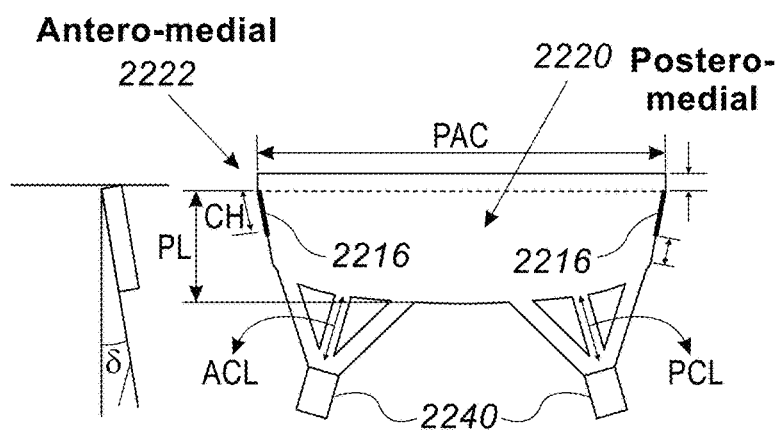
FIG. 22B
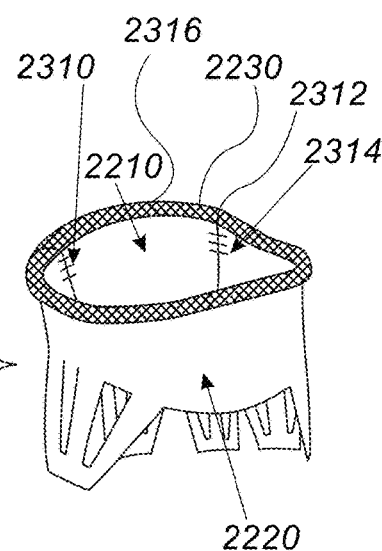
FIG. 22C

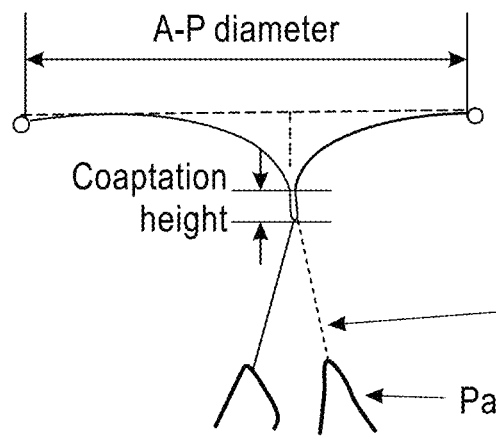
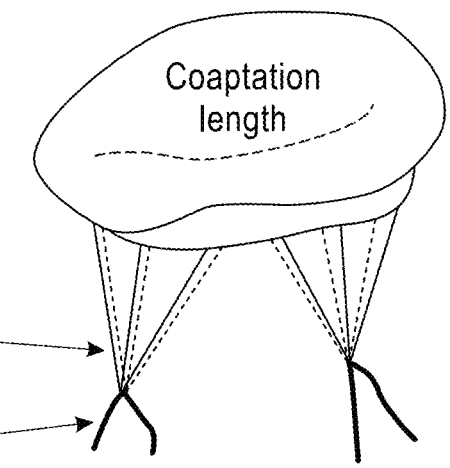
FIG. 24B
FIG. 24C
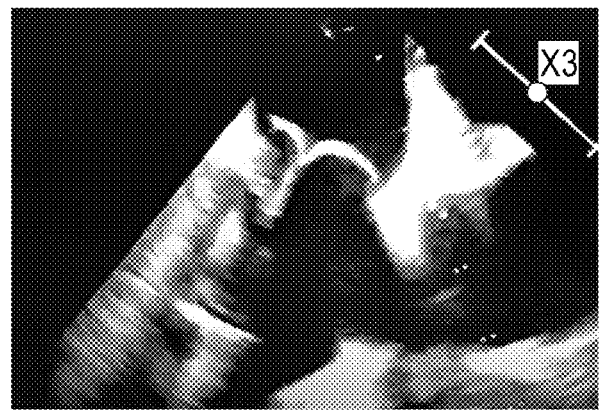
FIG. 25

METHOD FOR MANUFACTURING PERSONALIZED NATURALLY DESIGNED MITRAL PROSTHESIS

RELATED APPLICATION

This application is a continuation-in-part of U.S. patent application Ser. No. 16/384,957, which claims priority from U.S. patent application Ser. No. 15/766,377 published as U.S. Patent Publication No. 20180289484, which claims the benefit of U.S. Provisional Application No. 62/239,036, filed on Oct. 8, 2015. The entire teachings of the above application are incorporated herein by reference.

BACKGROUND OF THE INVENTION

The mitral or left atrioventricular valve, which is a bicuspid valve (i.e., a valve comprising two leaflets), is a valve in the heart that separates the left atrium and the left ventricle. The mitral valve allows blood to flow from the left atrium to the left ventricle during ventricular diastole, while preventing retrograde flow during systole. Naturally occurring mitral valve consists of an annulus, two leaflets, atrial myocardium, chordae tendinae, pupillary muscles and ventricular myocardium.

Mitral valve replacement is a procedure designed to be performed so as to replace a diseased or non-functioning valve. During the mitral valve replacement procedure, the patient's mitral valve is removed and is replaced with a prosthesis. The mitral valve unique configuration presents challenges for creating a long lasting and normally functioning mitral valve prosthesis.

Biological and mechanical mitral valve prostheses are available commercially. In contrast to the soft tissue and asymmetrical shape of the human mitral valve, both biological prostheses and mechanical prostheses have rigid, circular shapes. An additional disadvantage of mechanical valves is that blood has a tendency to clot on the mechanical components of the valve and cause the valve to function abnormally. Patients with mechanical valves must take anticoagulants to prevent the risk of blood clots forming on the valve, which can cause a stroke. Biological valves carry a reduced risk of forming blood clots but have more limited durability as compared with mechanical valves and require more frequent replacement. Biological valves, as do mechanical valves, include a rigid metal skeleton, and feature a metal ring covered with silicon or other synthetic material to allow passing of the implantation sutures.

Currently available mitral valve prostheses are typically built in an unnatural, circular-shaped manner and are often made of rigid materials. They also often feature three symmetric leaflets, whereas a natural human mitral valve includes only two leaflets, a larger anterior leaflet and a smaller posterior leaflet. Due to their rigid and unnatural construction, such mitral valve prostheses distort the natural anatomy of the heart. The heart muscle surrounding these prostheses does not recover well following implant surgery. The prostheses last an average of only 7-10 years, causing patients to require second and, sometimes, third surgeries during their life span, which repeatedly exposes patients to the high risks of open heart surgery.

Commercially available prostheses do not achieve the hemodynamic performance of a healthy native human mitral valve. This results in substantial energy loss of the left heart chamber, significant strain over time and finally heart failure and other adverse phenomena.

Some other available mitral valve prostheses may be formed by reinforcing a homograft as described in U.S. Pat. No. 6,074,417, which means the physician is required to scan various sizes of valves in order to find the best match per patient, while sacrificing animals from which the valves are to be taken. Yet other available mitral valve prostheses may be formed by sewing multiple layers of pericardium to one another, as described in U.S. Pat. No. 5,415,667, which may cause clotting in the areas where multiple sutures are present.

Other forms of atrioventricular valves, including mitral valves, are disclosed in U.S. Pat. No. 6,358,277 in which a template of membrane material is sutured onto the patient's mitral annulus. Such valves feature a high and unnaturally shaped annulus, making the circumference of the prosthetic valve bulky and raised like a collar. Moreover, templates are provided in standard sizes which must then be trimmed to adapt to a patient.

SUMMARY OF THE INVENTION

A method for manufacturing a personalized naturally designed mitral valve prosthesis that precisely fit and function per an individual patient is provided. Specifically, the method includes a series of operations or procedures beginning with receiving customized order of a mitral valve prosthesis with diagnosing imaging and analyzing imaging results, quantifying the valve prosthesis geometry and dimensions by using a validated algorithm, producing the valve according to the individualized geometry and dimensions of the recipient patient and assembling into a personalized valve prosthesis that is specially made to fit each specific patient's anatomy and clinical conditions, and further packaging and sterilizing the personalized valve prothesis into a final mitral valve prosthesis, sending for implantation into the specific patient and implanting the personalized prosthesis mitral valve into the patient.

A method for manufacturing a personalized naturally designed mitral valve prosthesis to precisely fit a specific patient for which the valve prosthesis is made for is provided. The method may comprise: measuring size and shape of a native mitral valve of the specific patient by using imaging methods, calculating geometry and dimensions of an annular ring, an anterior leaflet, a posterior leaflet and chords per the specific patient, based on validated algorithms, and cutting and connecting the annular ring, the anterior leaflet, the posterior leaflet and chords, thereby forming a personalized prosthesis mitral valve.

According to some embodiments, the imaging methods may comprise: 2D or 3D echocardiography, computed tomography (CT), Cardiac magnetic resonance (CMR) or any combination thereof.

According to some embodiments, measuring size and shape of a native mitral valve of a patient may comprise measuring mitral valve related parameters, the parameters may comprise: annulus circumference (AC), annulus area (AA), anterior-posterior (A-P) diameter, anterolateral-posteromedial (AL-PM) diameter, commissural diameter (C-C), anterior leaflet length (AL), posterior leaflet length (PL), mitral valve shape, and length of chordae tendineae (ACL and PCL).

According to some embodiments, the method may further comprise collecting physical information of the specific patient for use during calculating to predict the geometry of heart after implantation with improved heart valve function, said physical information comprising: body height, body weight, age, race and gender.

A personalized mitral valve prosthesis comprising a flexible annular ring dimensioned to match the native mitral annulus of a specific patient, a flexible anterior leaflet and a flexible posterior leaflet dimensioned to match the native mitral leaflets of the specific patient, the leaflets connected to the annular ring and chords dimensioned to match the native mitral leaflets of the specific patient, the chords to connect with papillary muscle of the heart is provided. The personalized mitral valve prosthesis may be formed by:

measuring size and shape of a native mitral valve of the specific patient by using imaging methods:

calculating geometry and dimensions of annular ring, leaflets and chords per the specific patient based on validated algorithms; and cutting and connecting the annular ring, leaflets and chords, thereby forming a personalized prosthesis mitral valve.

According to some embodiments, the imaging methods may comprise: 2D or 3D echocardiography, computed tomography (CT), Cardiac magnetic resonance (CMR) or any combination thereof.

According to some embodiments, measuring size and shape of a mitral valve of a patient may comprise measuring mitral valve related parameters, the parameters may comprise: annulus circumference (AC), annulus area (AA), anterior-posterior (A-P) diameter, anterolateral-posteromedial (AL-PM) diameter, commissural diameter (C-C), anterior leaflet length (AL), posterior leaflet length (PL), mitral valve shape, and length of chordae tendineae (ACL and PCL).

According to some embodiments, the personalized mitral valve prosthesis may further be formed by comprising collecting physical information of the specific patient for use during calculating to predict the geometry of heart after implantation with improved heart valve function, said physical information comprising: body height, body weight, age, race and gender.

According to some embodiments, the calculating may comprise calculating the annular ring circumference (AC) as a combination of anterior leaflet annular ring circumference (AAC) that is a top edge of the anterior leaflet, and posterior leaflet annular ring circumference (PAC) that is a top edge of the posterior leaflet based on equation (iii) hereinbelow. According to some embodiments, the annular ring may be formed into a multi-layered reinforced structure by folding or overlapping the top edge of each of the anterior leaflet and posterior leaflet.

According to some embodiments, the top edge of each of the anterior leaflet and the posterior leaflet may be straight or curved for properly fitting the personalized mitral valve prosthesis to the natural geometry of the left ventricle of the specific patient.

According to some embodiments, connecting may comprise joining the edge of the anterior leaflet with the edge of the posterior leaflet such to create a coaptation between the anterior leaflet and posterior leaflet. According to some embodiments, the coaptation may control the function and performance of the personalized mitral valve prosthesis by controlling the size of valve orifice and thus affect the trans-mitral pressure gradient.

According to some embodiments, connecting may comprise joining the two leaflets together thereby forming two commissures, wherein the two commissures incline inward in cone angle ($\delta_1$) to create a slight cone shape to the body of the personalized mitral valve prosthesis to properly fit in the native left ventricle per shape and contour of the specific patient.

According to some embodiments, the cone angle ($\delta_1$) may be determined by an inclined angle ($\delta_0$) of each commissure edge of the two leaflets based on equation (x).

According to some embodiments, connecting may comprise connecting the anterior leaflet to the posterior leaflet by connecting anterolateral side to anterolateral side and connecting posteromedial side to posteromedial side.

According to some embodiments, connecting the anterior leaflet to the posterior leaflet may be by stitching.

According to some embodiments, the measuring may comprise measuring: size and shape of a native annular ring of the specific patient, commissure height (CH) inclined angel ($\delta_0$), anterior leaflet length (AL) and posterior leaflet length (PL), and coaptation height (Coapt H) for calculating length of each leaflet edge based on equation (xi) hereinbelow.

According to some embodiments, the reinforced annular ring height may be between 1 mm and 4 mm.

According to some embodiments, the reinforced annular ring height may be between 2 mm and 3 mm.

According to some embodiments, the annular ring circumference (AC) may be a function of the anterior-posterior diameter (A-P) and the anterolateral posteromedial diameter (AL-PM) based on equation (iii) hereinbelow.

According to some embodiments, measuring the anterior-posterior diameter (A-P) and the anterolateral posteromedial diameter (AL-PM) may be when the mitral valve closes during left ventricular systole.

According to some embodiments, calculating the annular ring circumference (AC) of the prosthesis may be based on the annular ring width (d) of preserved native leaflets during clinical surgery.

According to some embodiments, calculating the annular ring circumference (AC) of the prosthesis may be based on a ratio ($\lambda$) in equation (iii).

According to some embodiments, the annular ring may be asymmetrical. According to some embodiments, the annular ring may be formed from a combination of an anterior leaflet annulus and a posterior leaflet annulus, whereby anterior leaflet annular circumference (AAC) may be smaller than posterior leaflet annular circumference (PAC), and the ratio (R) between AAC/PAC may be between 49/51 and 30/70.

According to some embodiments, ratio (R) between AAC/PAC may be between 35/65 and 42/58.

According to some embodiments, ratio (R) between AAC/PAC may be 40/60.

According to some embodiments, ratio (R) between AAC/PAC may be between anterior leaflet length (AL) and posterior leaflet length (PL) and may be crucial to ensure the prosthesis valve opens and closes properly.

According to some embodiments, calculating may comprise calculating the anterior leaflet length (AL) and posterior leaflet length (PL) based on: (a) an anterior-posterior diameter (A-P) that is a theoretical minimum distance for coaptation, (b) a ratio (r) between AL to PL, (c) coaptation depth (Cd), (d) the coaptation height (Coapt H) and (e) chord length (Lc) based on equations (viii) and (ix) hereinbelow, respectively.

According to some embodiments, connecting may comprise connecting the two leaflets together to form a body of the personalized mitral valve prosthesis.

According to some embodiments, each of the anterior leaflet and each of the posterior leaflet may comprise two sets of chords: anterolateral chords and posteromedial chords. According to some embodiments, each of the anterolateral chords and posteromedial chords may comprise three sub-chords, whereby the cords are uniformly distributed along at least ⅜ of each edge from each end.

According to some embodiments, calculating may comprise calculating length of each chord to ensure the personalized mitral valve prosthesis opens and closes properly, whereby calculating length of each chord is based on several parameters comprising: leaflet length, coaptation height, and coaptation depth.

According to some embodiments, measuring may comprise measuring distance from the papillary muscle apex to the coaptation edge to denote the prosthesis chord length, further comprising on-site measuring and adjusting of a pledget like chord cap into which the chords are integrated and merged at an end of each set of chords.

According to some embodiments, the personalized mitral valve prosthesis may further be formed by implementing calculated geometry and dimensions of annular ring, anterior leaflet, posterior leaflet and chords per the specific patient as inputs for an engineering drawing software or drawing tools.

According to some embodiments, the engineering drawing software or drawing tools may output a template for manually cutting the leaflets of the valve prosthesis.

According to some embodiments, the engineering drawing software or drawing tools may output a template for machine cutting the leaflets.

According to some embodiments, the personalized mitral valve prosthesis may further be formed by packing, labelling and sterilizing the personalized mitral valve prosthesis before release for usage.

According to some embodiments, the personalized mitral valve prosthesis may further be formed by assembling the personalized mitral valve prosthesis onto a valve holder before packaging.

According to some embodiments, the personalized mitral valve prosthesis may further be formed by implanting the personalized mitral valve prosthesis into the specific patient.

A prosthetic valve designed to resemble a patient's natural mitral valve is provided. Two flexible leaflets and an asymmetric and flexible ring can move with the natural distortion of the heart muscle during a cardiac cycle. Cords, similar to the native chordae tendineae of the patient, are included in the prosthetic valve to mimic the natural prevention of backflow of blood into the atria and to provide support to the left ventricle during systole.

According to some embodiments, a mitral valve prosthesis to be transplanted in a heart, includes:

an asymmetrical ring, the asymmetrical ring is dimensioned to mimic a native mitral annulus of a patient, the asymmetrical ring is constructed from a flexible material rolled onto itself towards the outer side of the valve:

an anterior flexible leaflet and a posterior flexible leaflet, the anterior and posterior leaflets suspended from the asymmetrical ring and configured to substantially coapt with each other;

each of the anterior and posterior leaflets shape is configured to mimic the shape of a native mitral valve, whereby the anterior and posterior leaflets create an orifice through which blood flows in one direction; and at least two sets of cords, each set of cords attached to the anterior or posterior leaflet on a first end and attached into a cap on a second end, the cap is configured to be attached onto papillary muscles of the heart on another end of the cap.

According to some embodiments, the mitral valve prosthesis may further comprise a coaptation surface continuing each one of the anterior and posterior leaflets and attached to each set of cords, the coaptation surface configured to enhance sealing of the mitral valve prosthesis.

According to some embodiments, the asymmetrical ring may further comprise at least two strands constructed in a coiled coil structure.

According to some embodiments, the asymmetrical ring may comprise two layers of material folded together to provide elasticity, and a third layer to provide structural stability.

According to some embodiments, the asymmetrical ring may comprise two layers of bovine pericardium; and a third layer of Glycine or Proline to provide strength.

According to some embodiments, the layers may be connected together via sutures stapler pins, glue or any combination thereof.

According to some embodiments, the asymmetrical ring, the anterior flexible leaflet and the posterior flexible leaflet, the at least two cords, the cap or any combination thereof may be made of bovine pericardium.

According to some embodiments, the leaflet shape may be extended by 1-5 mm to allow better coaptation and cord attachment.

According to some embodiments, the leaflet shape may be designed in a semicircular fashion along half of the length of the anterior flexible leaflet and the posterior flexible leaflet such that both leaflets create an 'S' shaped seal when coapted.

According to some embodiments, the mitral valve may further comprise at least one secondary cord: wherein the at least one secondary cord may be attached on one end to a mid-section of the posterior leaflet and on the other end to a mid-section of the primary cord.

According to some embodiments, the at least two sets of cords may be attached to an opening of the cap, the opening located in the middle of the cap.

According to some embodiments, each of the at least two sets of cords may be attached to a mid-section of the anterior or posterior leaflet such to mimic a naturally occurring mitral valve.

According to some embodiments, the anterior and posterior leaflets may be made of a single unit, connected to the asymmetrical ring and attached to at least two sets of cords.

According to some embodiments, the mitral valve may further comprise an extension connected on one end to the anterior flexible leaflet and on the other end to at least two sets of cords, and configured to allow coaptation between the anterior flexible leaflet and the posterior flexible leaflet.

According to some embodiments, a mitral valve prosthesis to be transplanted in a heart, may comprise:

an asymmetrical ring dimensioned to mimic a native mitral annulus of a patient: the asymmetrical ring is constructed from a flexible material rolled onto itself towards an outer side of the valve;

two leaflets suspended from the asymmetrical ring, said leaflets constructed on opposite sides of an incision made along a material similar to the material the asymmetrical ring is constructed from, wherein the incision creates an orifice through which blood flows in one direction;

at least two sets of cords, each set of cords attached to one of the two leaflets on a first end, and attached into a bundle on a second end, and a cap to be connected to the at least two sets of cords on one end of the cap and configured to be sutured onto papillary muscles of the heart on another end of the cap.

According to some embodiments, each set of cords is attached to one of the two leaflets via extensions configured to allow coaptation between the two leaflets.

According to some embodiments, a method of fabricating a mitral valve prosthesis may comprise:
measuring size and shape of a mitral valve of a patient, via imaging methods;
cutting a replica of the mitral valve of a subject from a single piece of material:
cutting an incision along the single piece of material, thus creating an orifice for blood flow and two leaflets, one on each side of the orifice:
measuring length of required cords via imaging methods:
attaching the cords to one of two caps: and
attaching a flexible ring onto the leaflets, thereby creating an entire mitral valve prosthesis, which mimics a native mitral valve of a specific patient.

According to some embodiments, measuring length of the required cords may be performed at the same time as measuring size and shape of a mitral valve of a subject.

According to some embodiments, the method may further comprise attaching extensions to each of the two leaflets to carry the cords prior to attaching the cords to one of two caps.

BRIEF DESCRIPTION OF THE DRAWINGS

FIG. 1A depicts a prosthetic mitral valve in an open position and shows chordae prior to attachment to the leaflets, in accordance with some embodiments of the disclosure. FIG. 1B depicts a prosthetic mitral valve in a closed position and shows chordae following attachment to the leaflets, in accordance with some embodiments of the disclosure;

FIGS. 15A-15B are schematic illustrations of extensions attached to the anterior leaflet and to the posterior leaflet, respectively, in accordance with some embodiments of the disclosure:

FIGS. 16A-16B are schematic illustrations of side-views of the mitral valve prosthesis with extensions and attached cords, during diastole and systole, respectively, in accordance with some embodiments of the disclosure;

FIG. 21A is a schematic illustration of a ring shaped valvular edge preserved when removing the native mitral valve in clinical practice, in accordance with some embodiments of the disclosure;

FIG. 21B is a schematic illustration of an ellipse shape annulus model with AL-PM diameter as major axis and A-P diameter as minor axis used to calculate annular circumference (AC) of the valve prosthesis, in accordance with some embodiments of the disclosure;

FIGS. 22A-22C are schematic illustration of an example design of anterior leaflet, an example design of posterior leaflet, and an example design mitral valve prosthesis assemble, respectively, in accordance with some embodiments of the disclosure:

FIGS. 24B-24C are schematic illustrations of side view and perspective view, respectively, of coaptation of mitral valve leaflet, in accordance with some embodiments of the disclosure; and FIG. 25 is a photograph of an echocardiography of an ovine heart implanted with a personalized naturally designed mitral valve prosthesis that is manufactured according to the method disclosed in the present disclosure.

Figure 1A:
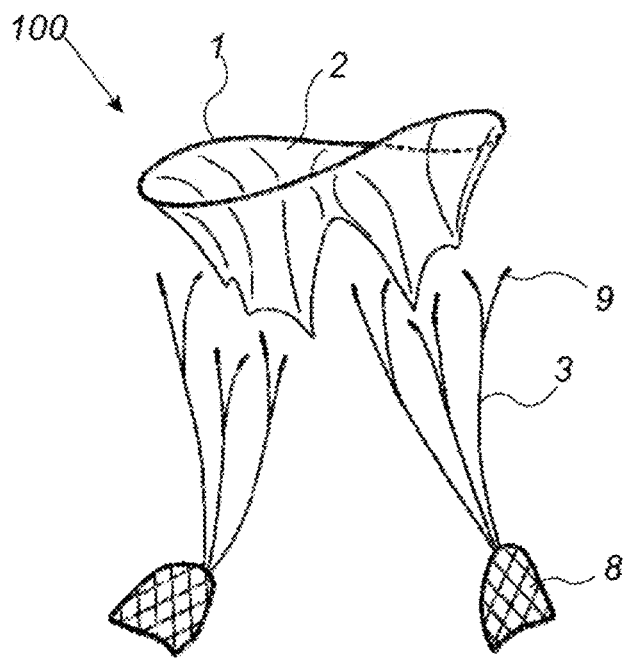
FIGS. 1A and 1B are schematics of embodiments of the present invention.

The foregoing will be apparent from the following more particular description of example embodiments of the invention, as illustrated in the accompanying drawings in which like reference characters refer to the same parts throughout the different views. The drawings are not necessarily to scale; emphasis instead being placed upon illustrating embodiments of the present invention.

DETAILED DESCRIPTION OF THE INVENTION

Figure 1B:
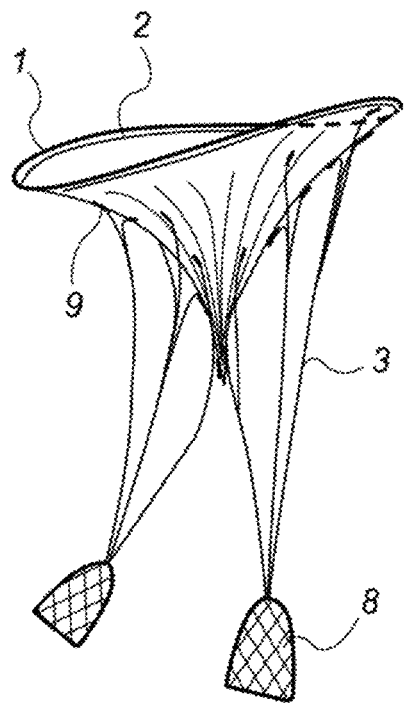

A mitral valve prosthesis of the invention is shown in FIGS. 1A and 1B. The mitral valve prosthesis 100 has a physiological shape that is similar to a natural human mitral valve. The mitral valve prosthesis includes a flexible, asymmetrical ring 1 and two flexible, membrane-like leaflets 2 that are suspended from the asymmetrical ring 1. The mitral valve prosthesis also includes two sets of cords 3 which mimic the chordae tendineae of the heart. Each set of cords 3 is configured to be attached to the margins and/or the bodies of the leaflets 2 at one end, and converge into a fixation cap 8 on the other end. Fixation caps 8 are configured to be sutured on to the papillary muscles of the left ventricle.

The mitral valve 100 is shown with the cords 3 unattached to the leaflets 2 in FIG. 1A and attached in FIG. 1B. The cords 3 may be attached to the leaflets 2 before surgery, or they may be attached during surgery. For example, attachments 9 between cords 3 and leaflets 2 may be sutures or they may be en-block engineered. Mitral valve 100 is shown in an open state in FIG. 1A and a closed state in FIG. 1B. In the closed state, leaflets 2 are shown to coapt.

Figure 2:
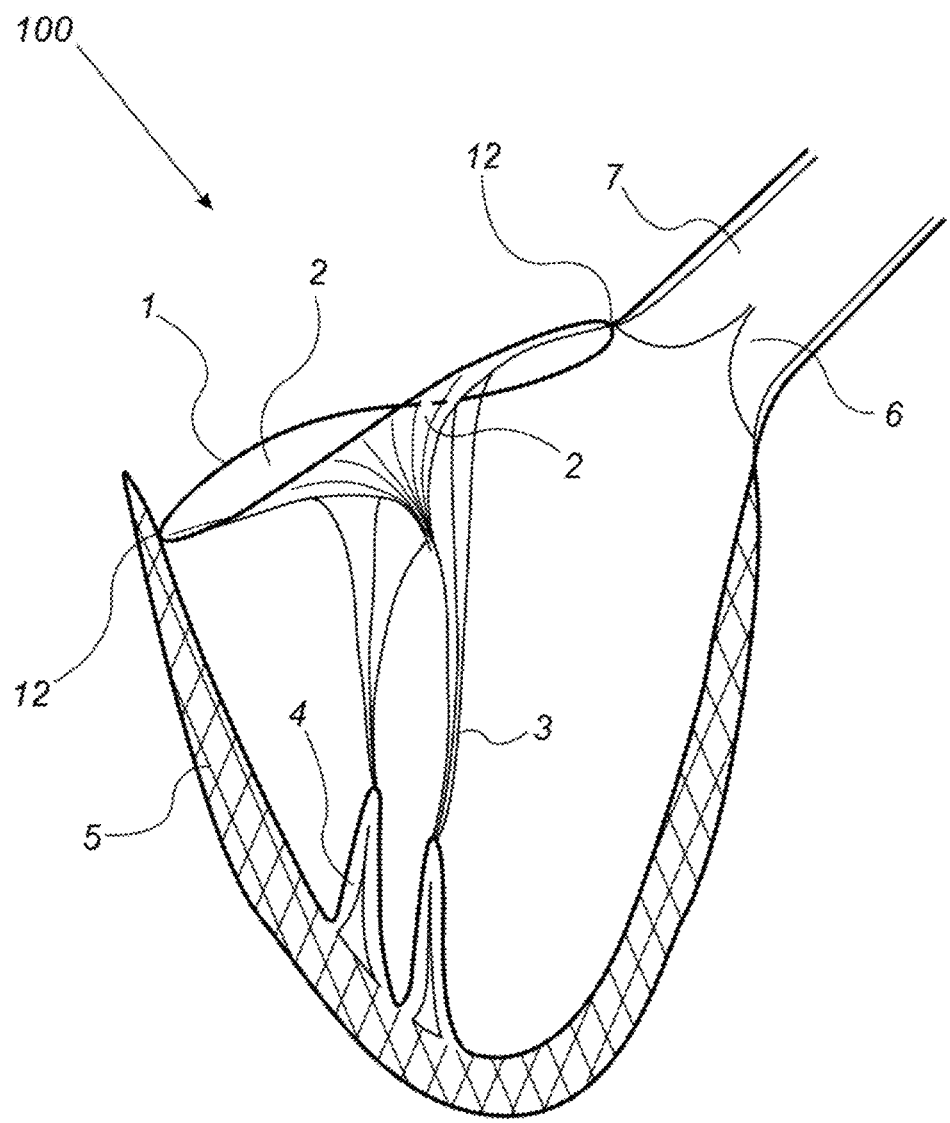
FIG. 2 is a schematic of an embodiment of the present invention implanted into the heart, in accordance with some embodiments of the disclosure.

FIG. 2 illustrates mitral valve 100 implanted into the heart. The mitral valve 100 is shown implanted at the location of the native mitral annulus 12, with one side adjacent to the aortic valve 6, where the root of the aorta 7 connects with the left ventricle, and the other side against the opposing ventricular wall 5. Cords 3 are shown attached to the papillary muscles 4.

Flexible ring 1 can be custom-made following an ultrasound examination of a patient's heart. In particular, a three-dimensional echocardiography study can be performed to obtain detailed anatomical measurements and/or render a three dimensional model of the patient's heart from which a customized mitral valve can be produced. Leaflets 2 and cords 3 can also be customized based upon ultrasound imaging of the subject's native mitral valve and surrounding anatomy. Customized mitral valves can also be produced from data obtained by other imaging modalities which provide three-dimensional information, including cardiac CT and cardiac MRI. As such, mitral valve prostheses of the present invention can be selected or designed to match the patient's specific anatomy.

Flexible ring 1 can be formed from, for example, an elastic annuloplasty ring. Leaflets 2 can be formed from natural material or biocompatible composite material which can resist clotting and function similarly to a patient's native anterior and posterior leaflets. At least two sets of cords, attaching to one of the two leaflets on a first end and to the papillary muscles on a second end, are provided to function similarly to the patient's native chordae tendineae. Cords 3, tethering the leaflets 2 to the papillary muscles of the patient, provide support to the left ventricular wall throughout the cardiac cycle and prevent the leaflets from opening into the atrium cavity.

The mitral valve prosthesis 100, including the flexible ring 1, leaflets 2, and cords 3, appears and behaves similar to a healthy, native mitral valve. Additionally, mitral valve prostheses of the present invention can be produced with natural materials and can avoid the inclusion of foreign material, such as pledgets. Homograft material and/or composite material, including various combinations of homograft, xenograft and/or autograft material, can be used to fabricate the flexible ring, leaflets, cords, and caps. The material which forms the valve ring and the leaflets can include, but is not limited to, human, bovine or porcine pericardium, decellularized bioprosthetic material, woven biodegradable polymers incorporated with cells, and extracellular materials. Biodegradable natural polymers can include, but are not limited tofibrin, collagen, chitosan, gelatin, hyaluronan, and similar materials thereof. A biodegradable synthetic polymer scaffold that can be infiltrated with cells and extracellular matrix materials can include, but is not limited to, poly(L-lactide), polyglycolide, poly(lactic-co-glycolic acid), poly(caprolactone), polyorthoesters, poly (dioxanone), poly(anhydrides), poly(trimethylene carbonate), polyphosphazenes, and similar materials thereof. Flexible rings can be further customized to provide individualized flexibility or rigidity for the patient. Additionally, some components of the mitral valve prosthesis, including cords 3, can be fashioned intraoperatively by autologous pericardium of the patient.

For example, a mitral valve prosthesis can be fabricated from the patient's own pericardium. Alternatively, the mitral valve prosthesis can be fabricated from xenogeneic materials (e.g., animal tissues, such as existing valves) over which a layer of the patient's own cultured cells is applied by means of tissue engineering.

Artificial valves are frequently fixed with glutaraldehyde, which is a known toxin and promotes regeneration. Mitral valve prostheses of the present invention can be fixed by non-glutaraldehyde-based methods, such as dye-mediated photofixation. Mitral valves of the present invention can also be fixed by using alternative cross-linking agents, such as epoxy compounds, carbodiimide, diglycidyl, reuterin, genipin, diphenylphosphorylazide, acyl azides, and cyanamide, or by physical methods, such as ultraviolet light and dehydration.

Mitral valve prostheses, or some components of the prostheses, can be produced directly with biological three-dimensional (3D) printing using biological materials. Alternatively, mitral valve prostheses, or some components of the prostheses, can be produced using a template or mold constructed by three-dimensional printing, based on the detailed dimensions obtained from three-dimensional imaging performed pre-operatively.

A method of implanting a mitral valve prosthesis is also provided. Prior to implantation, an echocardiography study (or other imaging study) of the patient is obtained. From the imaging study, heart chamber sizes and movements are measured. The detailed dimensions of the patient's mitral annulus, leaflets and cords are also measured from the acquired images. Additionally, a three-dimensional depiction of the valve to be replaced can be rendered. From the measurements and three-dimensional modeling of the patient's native valve, a mitral valve prosthesis can be produced that closely matches the patient's native mitral valve corrected for the existing pathology.

A three dimensional echocardiography study can be performed with, for example, a transesophageal echocardiography (TEE) probe or a transthoracic echocardiography (TTE) probe. Segments of the mitral valve can be three-dimensionally and four-dimensionally modelled and measured using software such as eSieValves™ (Siemens Medical Solutions USA. Inc., Malvern, Pa.). Relevant measurements can include outer and inner diameters of the annulus, annular areas, intertrigonal and intercomm distances, and lengths along various axes of the anterior and posterior leaflets.

Figure 3:
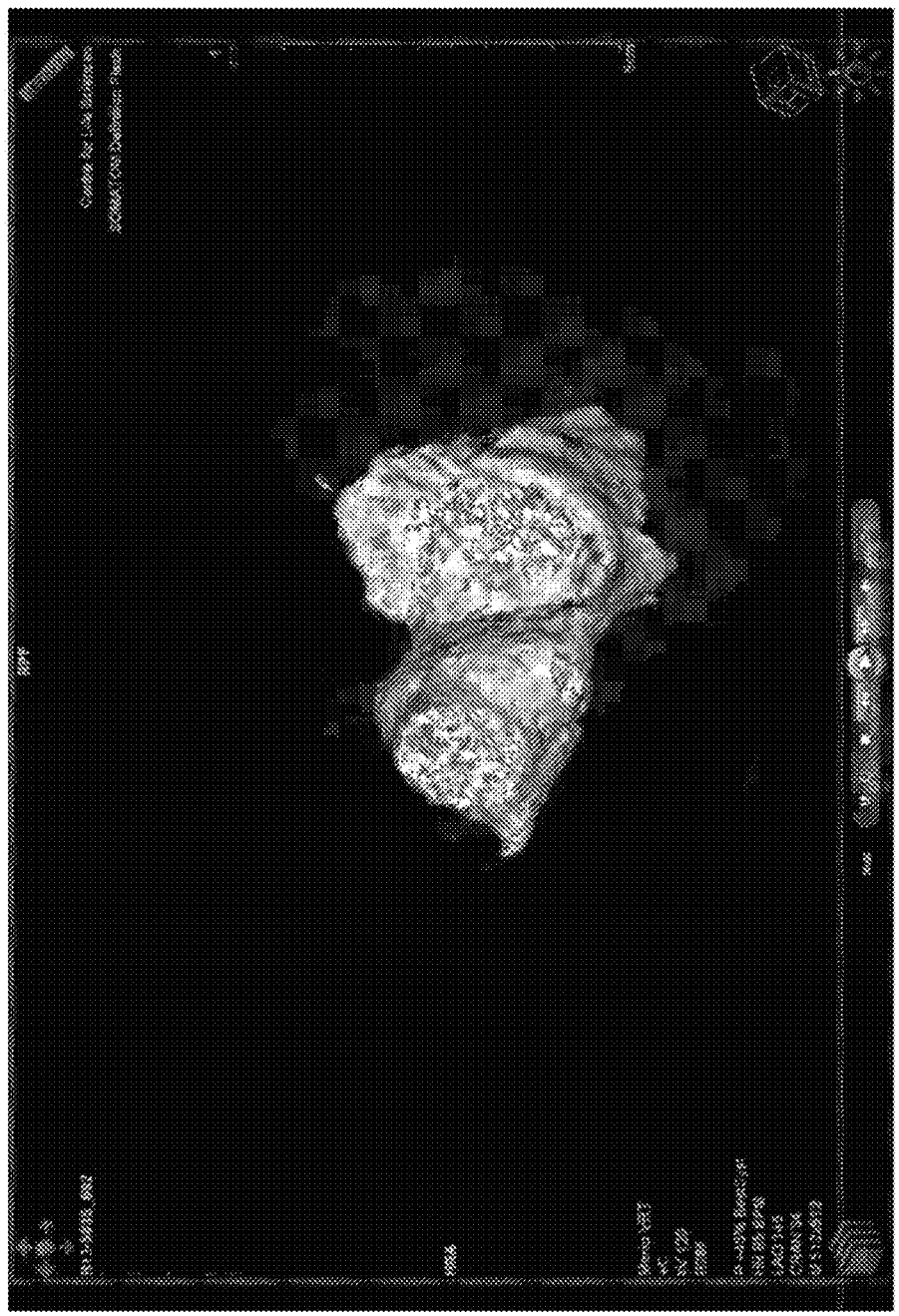
FIG. 3 is an image of a 3D reconstruction of a mitral valve area in 3D CT image analysis software, in accordance with some embodiments of the disclosure.

In addition, or alternatively, a three dimensional study of a mitral valve can be performed with computed tomography (CT) or magnetic resonance imaging (MRI). For example, as shown in FIG. 3, a 3D reconstruction of a porcine heart was obtained using CT imaging (SOMATOM® Definition Flash, Siemens Healthcare, Erlangen, Germany), with the mitral valve area of the heart visible on the right side of the image. Segmentation of the mitral valve area can be performed using the image analysis software and relevant measurements can be obtained.

Figure 4:
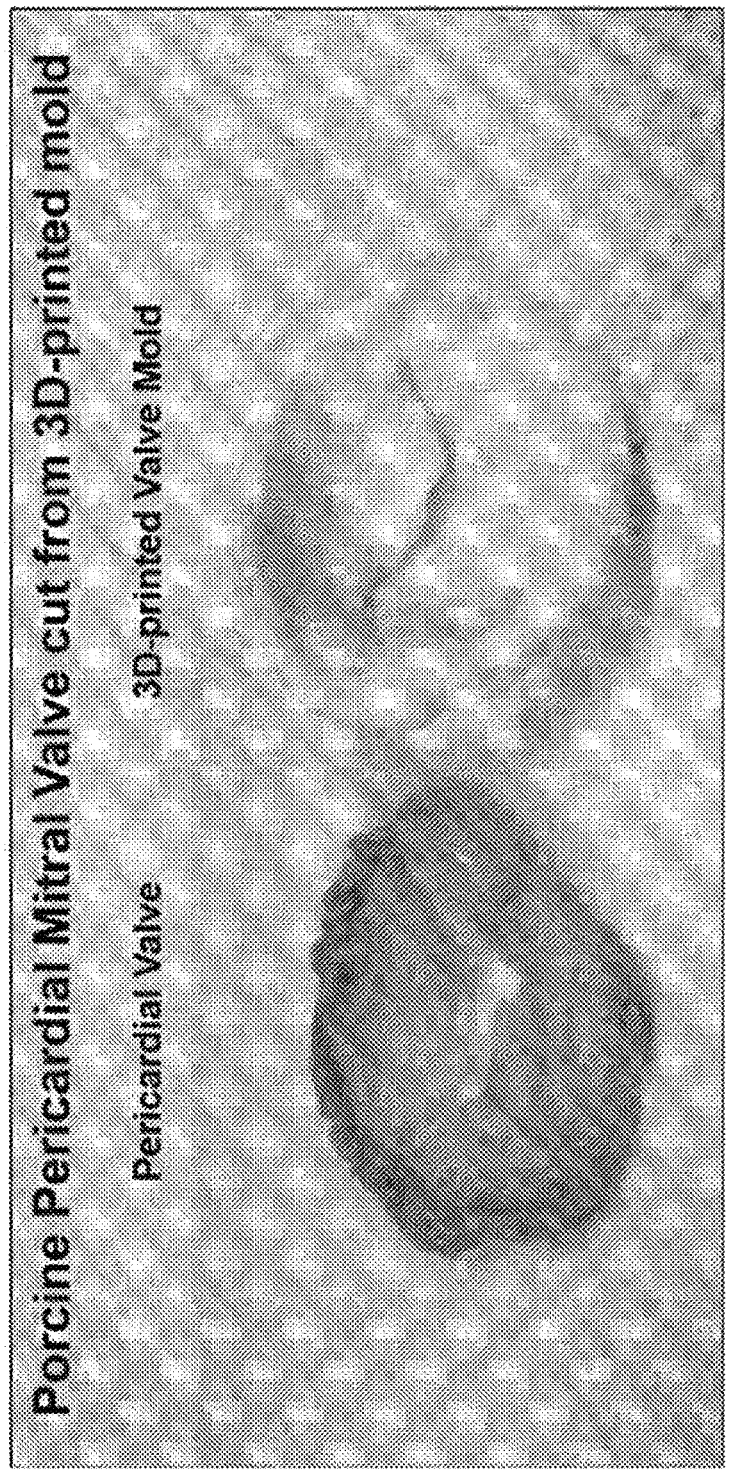
FIG. 4 is a photograph of a 3D printed valve mold and porcine pericardial mitral valve leaflets, in accordance with some embodiments of the disclosure.

The mitral valve prosthesis can be completely customized for a patient, with each component (e.g., ring, leaflets, cords, caps) fabricated to have dimensions that match those of the patient's native valve. For example, as shown in FIG. 4, a 3D printed mold of a mitral valve was created based on a 3D reconstruction of an imaged valve. The 3D printed valve shown in FIG. 4 was modeled during the diastolic, or opening, phase of the cardiac cycle. A prosthetic valve based on the 3D mold is also shown in FIG. 4. The mold can guide the cutting of porcine pericardium into leaflets and chordae attachment sites. Alternatively, a prefabricated mitral valve, or prefabricated components of a mitral valve, can be selected for implantation that are closest in shape and size to the patient's native valve or native valve components.

Figure 5:
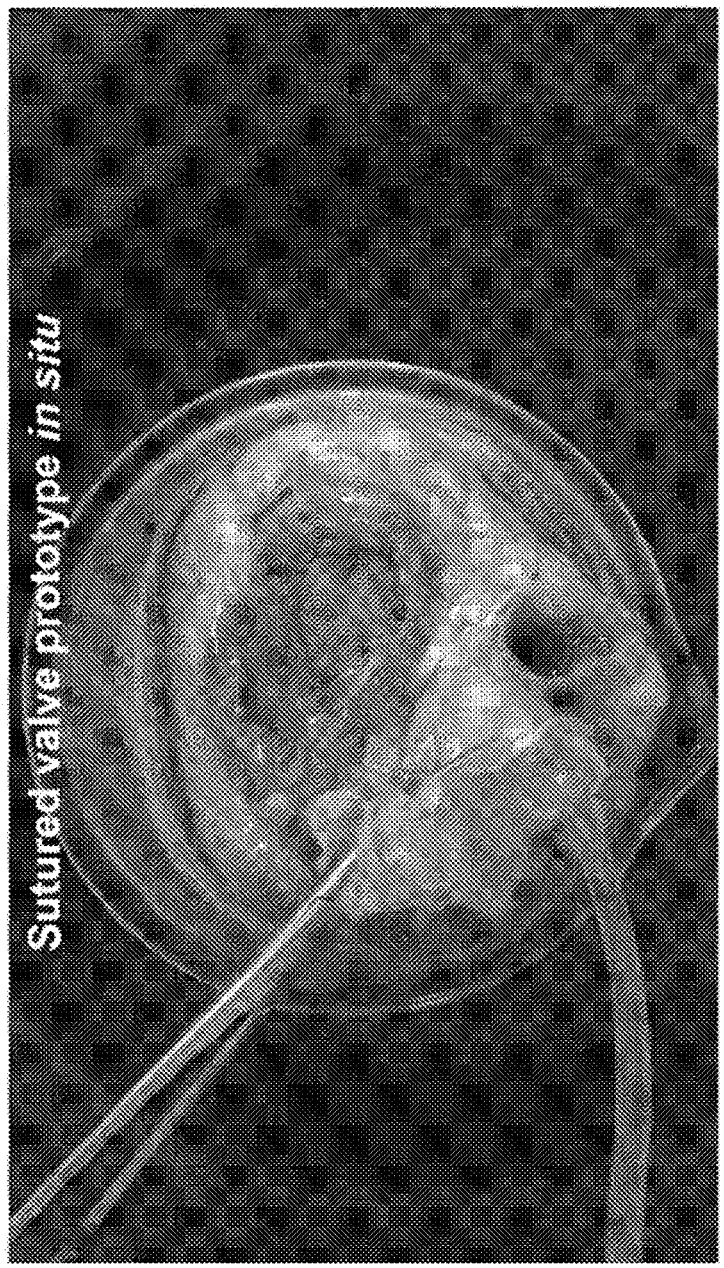
FIG. 5 is a photograph of a prosthetic valve under ex vivo testing, in accordance with some embodiments of the disclosure.

FIG. 5 shows an image of a prosthetic valve prototype sutured in an ex vivo testing system. The valve prototype is shown sutured to an explanted whole heart. Saline boluses are injected through a tube into the left ventricle of the heart with the aorta clamped to contain the saline in the left ventricle and to create pressure. The injection pressure can be monitored, for example, on a pressure gauge connected to the injection line. The competency of the valve prototype (e.g., absence of regurgitation and prolapse of the valve leaflets) under physiological pressure can then be monitored. Competency of the valve can be measured or monitored while the left ventricle is contracting and at the systolic pressure at which a native valve closes.

Figure 6A:
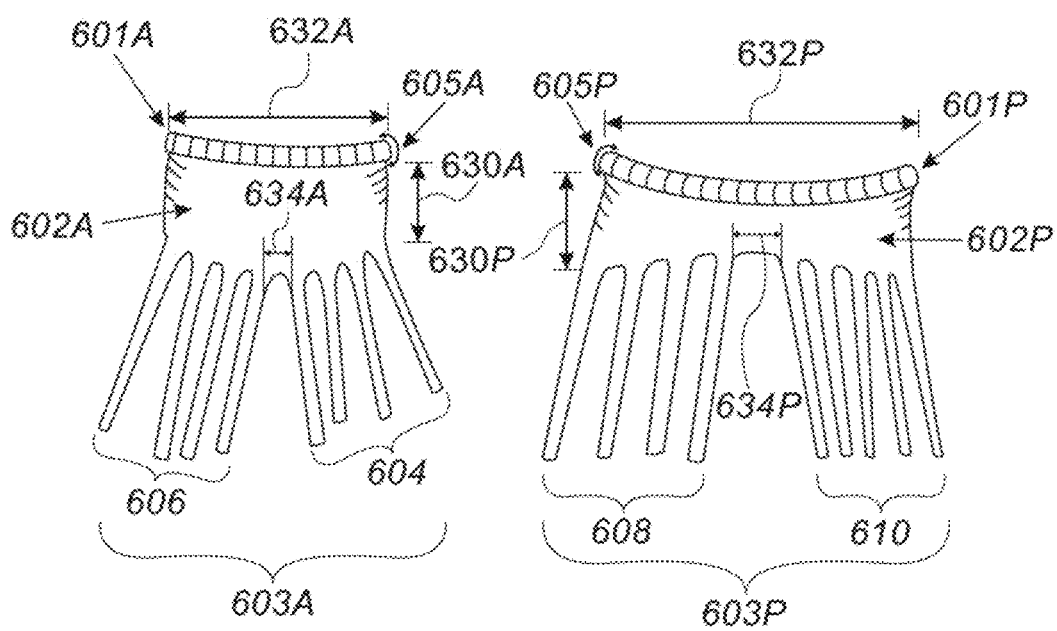
FIGS. 6A-6B are schematic illustrations of a side view of the anterior and posterior leaflets of a prosthetic mitral valve, and a top view of the leaflets when coapt with each other, respectively, in accordance with some embodiments of the disclosure.
Figure 6B:
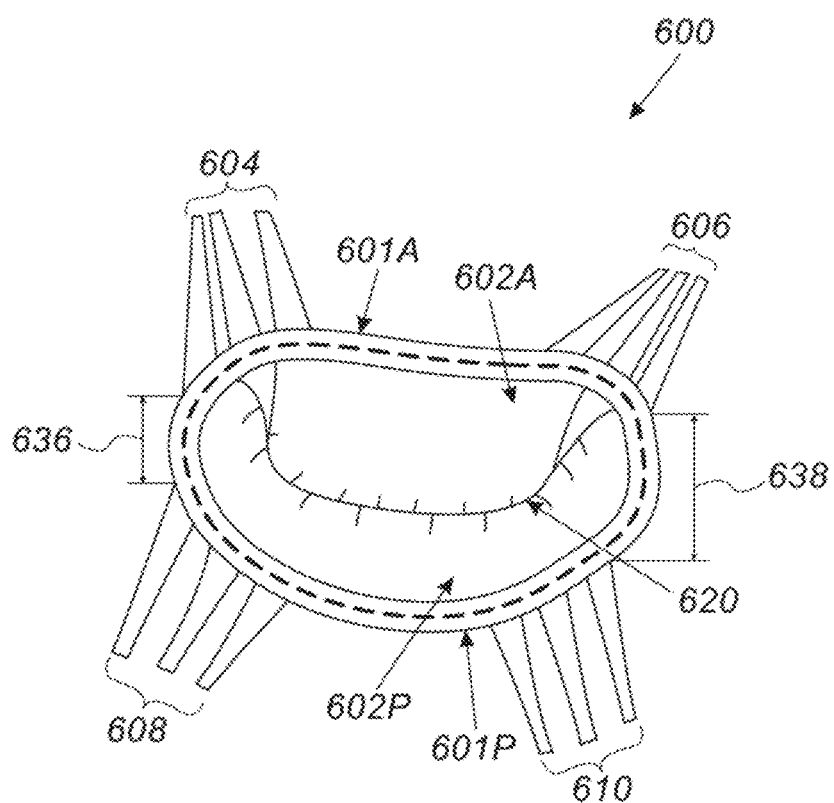

FIGS. 6A-6B are schematic illustrations of the anterior and posterior mitral leaflets of a prosthetic mitral valve, and the leaflets when coapt with each other, respectively, in accordance with some embodiments of the disclosure. According to FIGS. 6A and 6B the prosthetic mitral valve may be prosthetic mitral valve 600. According to some embodiments, valve 600 may comprise two leaflets, for example, anterior mitral leaflet 602A and posterior mitral leaflet 602P. Each of the mitral valve posterior and anterior leaflets 602P and 602A, respectively, may be designed and created pre-operation as a monocoque (single piece) to fit the patient's specific physiology and anatomy based on a cross sectional image of the heart of the patient. Measurements taken from the patient's own heart may be used to determine each of the leaflet's e.g., 602A, 602P length, width, and height such that each leaflet is substantially the same as the patient's natural leaflets. Each of the leaflets may be shaped to include chordae (e.g., chords 604, 606, 608, 610) and additional material so as to form a ring portion (e.g., anterior ring portion 601A and posterior ring portion 601P). The length of the chordae may be determined by the surgeon to fit the patient as is further described below. The leaflets may be cut from a single piece of material using a knife or scissors and may be sutured by the surgeon during the mitral valve replacement operation to form a mitral valve, which resembles the patient's natural mitral valve.

For example, the anterior leaflet (AL) height may be around 30 mm, the AL length may be around 45 mm, the posterior Leaflet (PL) height may be around 15 mm, and the posterior leaflet length may be around 60 mm. As illustrated in FIG. 6A, the medical community refers to 630A as the height of anterior leaflet 602A, and to 630P as the height of posterior leaflet 602P, while the length of each leaflet is referred to as the potion of the perimeter of the leaflet, e.g., 632A refers to the length of anterior leaflet 602A, and 632P refers to the length of posterior leaflet 602P.

According to some embodiments, cutting each of leaflets 602A and 602P separately from the same or different pieces of material, as well as cutting each of the ring portions 601A and 601P, separately, may ease on the person, e.g., the surgeon, who is preparing the prosthetic mitral valve for implantation. Cutting the leaflets as two separate portions as well as cutting the ring portions as two separate portions, and attaching the leaflets to the ring and further attaching cords to each leaflet, shortens the preparation time and the time needed to perform the surgical procedure of implanting the prosthetic valve compared to when the leaflets and cords are cut from a single piece of material as a single unit. Cutting the leaflets and cords as a single unit and implanting a single piece prosthetic is more complex and time consuming than the methodology disclosed herein due to the high accuracy required in cutting the leaflets and each of the cords, while maintaining the connection between the leaflets portion and the cords portion intact.

In some embodiments, each of ring portions 601A and 601P is created through rolling of each leaflet posterior side, such that each leaflet posterior side is folded or rolled onto itself (e.g., rolled anterior section 605A, and rolled posterior section 605P), towards the outer side of valve 600. According to this embodiment, the size of the posterior end of each leaflet may be increased by 5-10 mm of additional material, which may be used when rolling the posterior end of the leaflet onto itself to create the ring portion (such as ring portion 601A in the anterior mitral leaflet and ring portion 601P in the posterior mitral leaflet). Rolling or folding the ring (or each ring portion 601A and 601P) onto itself towards the outer side of valve 600 may assist in avoiding the creation of clots at the inner side of valve 600, and if clots are to be created, they would only appear on the outer side of valve 600 at the area of the fold or roll of the ring or ring portion, which poses less risk of damaging the efficient operation of valve 600. According to some additional embodiments, the ring (or each ring portion 601A and 601P) may be further strengthened by the additional of strips of material (not shown) such as suitable biomedical fibers or polymers. Such strips may be made from pieces of material from which valve 600 is made and dimensioned to fit within each ring portion 601A, 601P.) Preferably such strips have a width of 1-3 mm and length of 10-20 mm. Such strips of material may be added to the valve 600 when each ring portion 601A, 601P is rolled, said strips are placed within each ring portion 601A. 601P. These strips of material may be elastic and may be made of various compositions, such as biocompatible rubbers, recoiling metal wires or synthetic materials.

According to FIG. 6B, leaflet 602A may be in the shape of a half ellipsoid or piano-convex shape, while leaflet 602P may have a plano-concave shape. In some embodiments, valve 600 may comprise at least two sets of cords. In some embodiments, each of the at least two sets of cords is attached to a mid-section of a respective leaflet such to mimic a native mitral valve. For example, in some embodiments, leaflet 602A may comprise at least one set of cords 603A, which may be connected to a mid-section of leaflet 602A on one end of leaflet 602A, which is typically opposite the end where ring portion 601A is connected to leaflet 602A. In some embodiments, the at least one set of cords 603A may comprise at least two sub-sets of cords, for example, sub-set of cords 604 and sub-set of cords 606. According to some embodiments, these sub-sets of cords 604 and 606 are spaced such that a gap of about 3-5 millimeters is maintained between the two sub-sets of cords to enable a more efficient coaptation. The gap between the sub-sets of chords 604 and 606 also serves to create a more homogenous distribution of tension on the leaflets, and potentially diminishes wear and tear. These sub-sets of cords 604 and 606 may be connected to different and separate caps for connecting the sub-set of cords to papillary muscles of the heart, as will be explained in detail with respect to FIGS. 7A-7B.

In some embodiments, leaflet 602P may comprise at least one set of cords 603P, which may be connected to a mid-section of leaflet 602P on one end of leaflet 602P, which is typically opposite the end where ring portion 601P is connected to leaflet 602P.

In some embodiments, the at least one set of cords 603P may comprise at least two sub-sets of cords, for example, sub-set of cords 608 and sub-set of cords 610. These sub-sets of cords 608 and 610 are spaced such that a gap of about 5-8 millimeters is maintained is maintained between the two sub-sets of cords to enable a more efficient coaptation. These sub-sets of cords 608 and 610 may be connected to different and separate caps for connecting the sub-set of cords to papillary muscles of the heart, as will be explained in detail with respect to FIGS. 7A-7B.

In some embodiments, the width of cords 603A and/or cords 603P may be between 1 mm to 2 mm, though other widths may be implemented. In some embodiments, posterior mitral leaflet 602P may be connected on one side to a ring portion 601P of an asymmetrical ring. Once ring portion 601A is attached, e.g., via sutures, fasteners, etc. to ring portion 601P, a complete asymmetrical and flexible ring may be formed.

According to some embodiments, interchodal distance in anterior Mitral Leaflet 634A may be between 8-10 mm. In some embodiments, interchodal distance in posterior Mitral Leaflet 634A may be between 10-15 mm. In some embodiments, interchodal distance between the anterior and posterior leaflet in the commissure area, noted as distance 636 and/or 638 may be between 5-7 mm.

According to some embodiments, and as illustrated in FIG. 6B, anterior leaflet 602A may be connected to posterior leaflet 602P, and ring portion 601A may be connected to ring portion 601P in order to construct prosthetic mitral valve 600. An orifice 620 that is created between leaflet 602A and leaflet 602P once leaflet 602A is connected to leaflet 602P, may enable flow of blood in one direction, i.e., from the left atrium to the left ventricle. Accordingly, the orifice 620 created between leaflet 602A and leaflet 602P may be configured to prohibit backflow, i.e., from the left ventricle to the left atrium. Leaflet 602A, leaflet 602P and the way these leaflets are connected to one another with a certain coaptation, as well as ring portion 601A and ring portion 601P may be configured to mimic the shape, size and thus function of a natural human mitral valve. Specifically, ring portion 601A may be configured to mimic the anterior annulus, while ring portion 601P may be configured to mimic the posterior annulus of a natural mitral valve. In some embodiments, each leaflet may comprise a shape that is extended by approximately 1-5 mm located between the ring portions and the cords, in order to allow better coaptation between the two leaflets and better cord attachment to each of the leaflets.

In some embodiments, anterior leaflet 602A may comprise at least two sub-sets of cords, e.g., sub-set of cords 604 and sub-set of cords 606, which may be connected to leaflet 602A on different ends of leaflet 602A. In some embodiments, posterior leaflet 602P may comprise at least two sub-sets of cords, e.g., sub-set of cords 608 and sub-set of cords 610, which may be connected on different ends of leaflet 602P. As in a natural mitral valve, the cords should be connected to the papillary muscles of the heart. More specifically, in a natural human mitral valve, each sub-set of cords is attached to a different area of the papillary muscles. Thus, prosthetic valve 600 may comprise at least two sub-sets of cords per each leaflet, whereby each sub-set of cords is to be attached to a different papillary muscle area such as to closely mimic the configuration and thus operation of a natural mitral valve. As will be explained with respect to FIGS. 6C, and 7A-7B, each sub-set of cords may be connected to the papillary muscles via caps in order to ensure an easy yet sufficiently stable and durable attachment between any sub-set of cords and the papillary muscles. The number of cords in each sub-set of cords, e.g., 604, 606, 608 and 610 may be different or the same. In some embodiments, each sub-set of cords may include at least two cords.

Figure 6C:
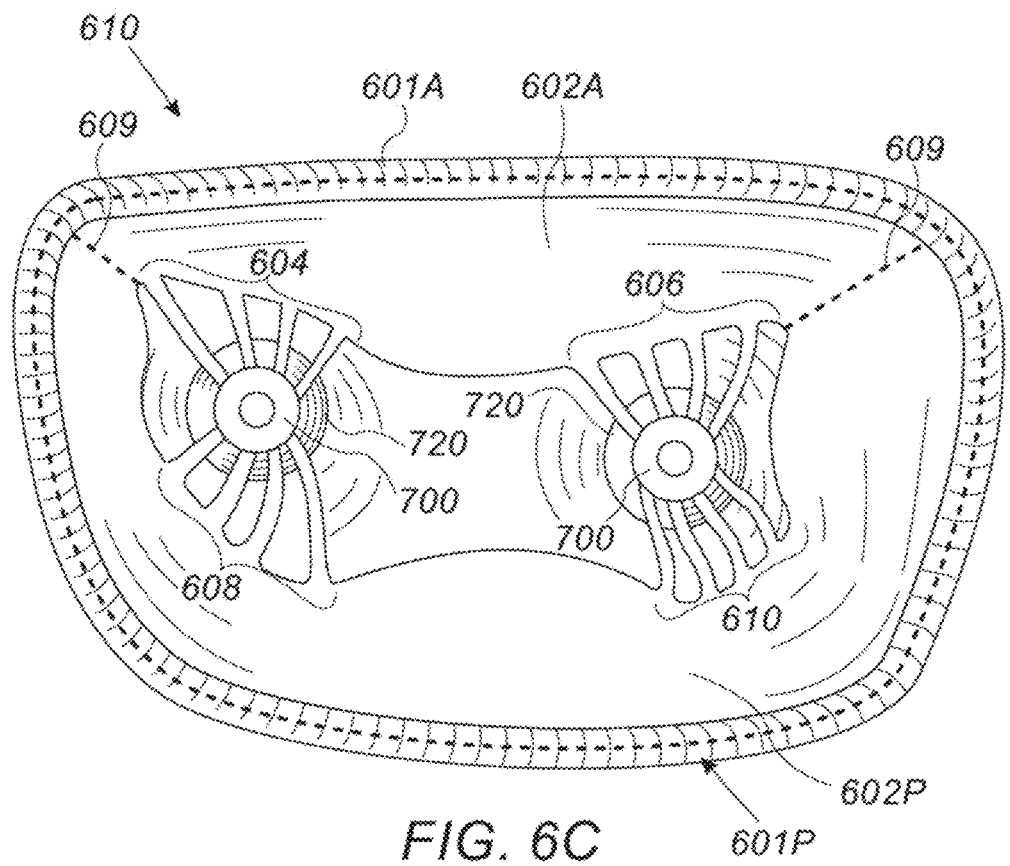
FIG. 6C is a schematic illustration of an upper view of the mitral valve prosthesis from the left atrium looking downwards towards the left ventricle (during diastole, when the valve is open to allow for blood to enter into the left heart ventricle), in accordance with embodiments of the present disclosure.

FIG. 6C is a schematic illustration of an upper view of the mitral valve prosthesis from the left atrium looking downwards towards the left ventricle, in accordance with embodiments of the present disclosure. According to FIG. 6C, the posterior leaflet 602P may be attached to anterior leaflet 602A via attachment lines, e.g., suturing lines 609. In some embodiments, ring portion 601A may be attached to ring portion 601P, e.g., along lines 609, and may be rolled onto itself towards the outer side of valve 600. In some embodiments, anterior leaflet 602A may comprise two sub-set of cords, e.g., sub set 604 and 606, whereby each of these sub sets of cords may be connected to a different papillary muscle 720 via a separate cap element 700. Accordingly, posterior leaflet 602P may comprise two sub-sets of cords 608 and 610, whereby each sub set of cords may be attached to the papillary muscles 720 via a different cap element 700. For example, anterior cords 604 may be connected via a first cap 700 to a first papillary muscle 720, while posterior cords 608 may also be connected via the same first cap 700 to the same first papillary muscle. Similarly, anterior cords 606 may be connected via a second cap 700 to a second papillary muscle 720, while posterior cords 610 may also be connected via the same second cap 700 to the same second papillary muscle.

Figure 6D:
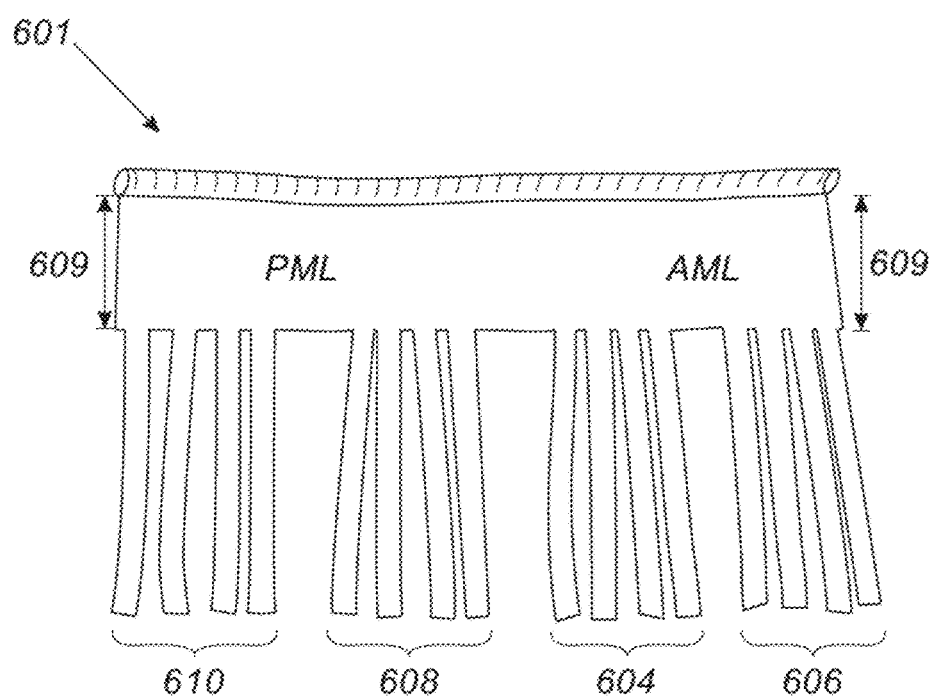
FIG. 6D is a schematic illustration of a single piece of material comprising the anterior and posterior leaflets, in accordance with embodiments of the present disclosure.

According to FIG. 6D, in some embodiments, leaflets 602P and 602A may be cut from a single monocoque and connection, e.g., suturing to form the complete valve may be performed along suturing lines 609. According to some embodiments, the cords may be adjusted per the individual optimal cord length of the recipient/patient, based on pre-operative scans of the patient.

Figure 7A:
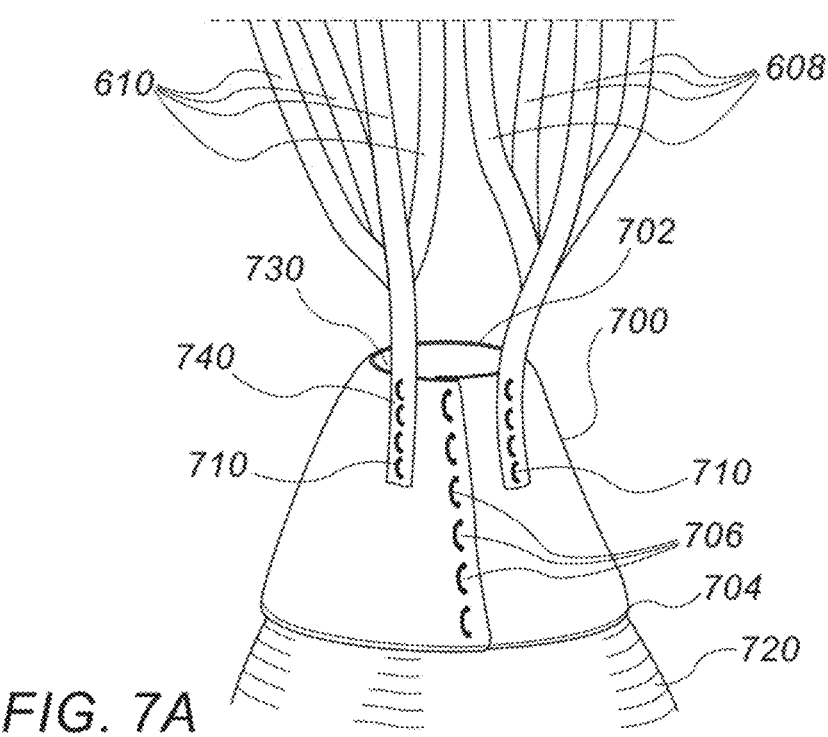
FIGS. 7A-7B are schematic illustrations of a cap for connecting the cords to the papillary muscles of the heart, and of a mitral valve prosthesis with two caps attached to the cords in accordance with embodiments of the present disclosure.
Figure 7B:
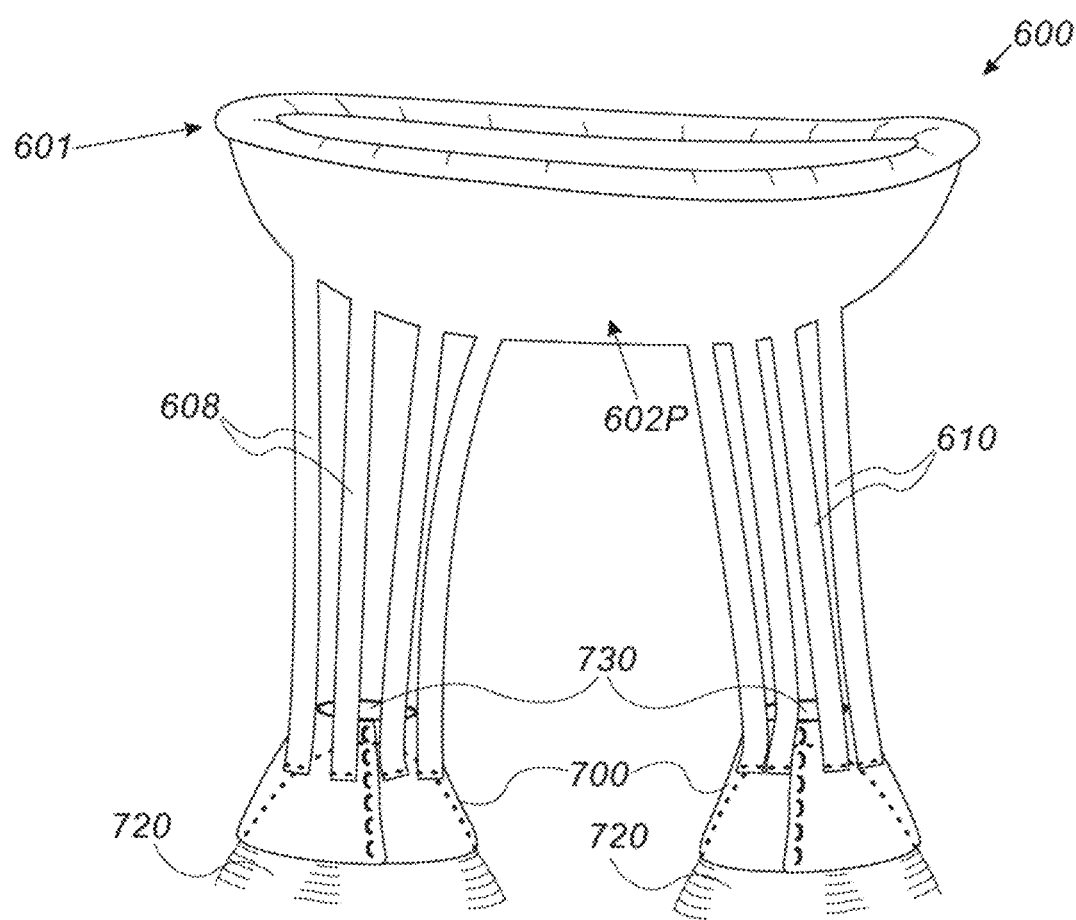

FIGS. 7A-7B are schematic illustrations of a cap for connecting the cords to the papillary muscles of the heart, and of a mitral valve prosthesis with two caps attached to the cords, respectively, in accordance with embodiments of the present disclosure. In some embodiments, the shape of cap 700 when in a layout configuration, may be in the shape of an arc. In some embodiments, the shape of cap 700 in closed configuration may resemble the shape of a tapered cone having a small opening 730 at its top end 702 and a wider opening at its bottom end 704, whereby the ends of the arc may be sutured to one another or one on top of the other, using surgical suturing 706, such to create the closed configuration. Sutures 706 may be performed prior to placing the cap 700 on top of pupillary muscles 720. In some embodiments, cap 700 may measure anywhere between 5 mm to 10 mm in diameter and 5-10 mm height. According to some embodiments, cap 700 may be made of a single piece of material in the shape of a cap, while according to other embodiments, cap 700 may be made of two open leaflets or pieces of the same material that are to be sewn together and onto the papillary muscle at once. For example, a suture may begin on one side of the two pieces of material of cap 700, and exit through a portion of cap 700, such to attach cap 700 onto the papillary muscle, and so on, until the two parts of cap 700 are fully connected to one another and to the papillary muscles of the heart.

According to some embodiments, cap 700 of the prosthetic valve 600 may be formed by rolling pericardium (e.g., from human source, bovine or porcine) to a closed configuration. In some other configurations the cap may be formed by a biomedical polymer. In some embodiments, the size of cap 700 may be 5 mm over 5 mm. In some embodiments, the chordae of the prosthetic mitral valve may be made of the same material as that of the leaflet and/or cap. In some embodiments, the chordae may be chordae taken from the same source from which cap 700, anterior leaflet 602A and posterior leaflet 602P are taken from, e.g., the same animal, for example the same cow, for adding the benefit of having the same cellular structure and same origin as cap 700, anterior leaflet 602A and posterior leaflet 602P.

Once cap 700 is placed onto pupillary muscle 720, cords, such as sub-set cords 604, 608, may be connected to the cap 700 using sutures 710, which may connect together the cords, cap 700 and pupillary muscle 720. According to some embodiments, cap opening 730 may enable achieving a good fit between cap 700 and the papillary muscle 720, since cap opening 730 makes it possible to adjust the shape of the cap to that of the papillary muscle 720. In some embodiments, cap 700 may be attached, e.g., via sutures 710, to sub-set cords 604, and 608 on one of its ends, while cap 700 may be attached, e.g., via sutures 706 to the papillary muscles of the heart from another, typically opposite end of cap 700, which is in close proximity to bottom end 704. Cap 700 may be connected to the papillary muscles 720 through the entire circumference of bottom end 704 of cap 700, though in some embodiments, cap 700 may be connected to the papillary muscles 720 via specific portions along the circumference of bottom end 704 of cap 700.

According to some embodiments, the cords may be connected to each other such to form a bundle of cords. The cords may be connected as a bundle at the end of the cords that is to be connected to cap 700 (e.g., the end of sub-set cords 604 and 608, connected to leaflet 602). According to some embodiments, connecting the cords, e.g., sub-set cords 604 and 608, to the papillary muscles 720 via cap 700 is easier than connecting the cords to the papillary muscles 720 directly, since it would require a more extensive attachment procedure. For example, if the attachment method is suturing, then suturing each one of the cords to the papillary muscles 720 is more complex and time consuming compared to suturing the cords to the laid out cap 700 and suturing cap 700, which is one single large piece, onto the papillary muscles 720. Since the patient receiving the prosthesis of the present disclosure is connected to a cardiopulmonary bypass, also commonly known as a heart-lung machine, it is preferable to conduct the mitral valve replacement with expediency.

While FIG. 7A shows only two sub-set cords 604, and two sub-sets cords 608 attached to cap 700, it should be appreciated that additional cords may be connected to cap 700. Sub-set cords 604, 608 may comprise one or more cords. In some embodiments, as shown in FIG. 6C, four cords 604 from the right scallop of the anterior mitral leaflet 602A and four cords 608 from the left scallop of the posterior mitral leaflet 602P are connected to cap 700.

In some embodiments, each of the sub-set of cords 604, 606, 608 and 610 may be connected to cap 700 along the external side of cap 700. In other embodiments, the cords or at least some of the cords of the prosthetic valve may be attached to cap 700 via opening 730, which may be located at the middle of cap 700. That is, the cords may pass through opening 730 and may be attached to the inner side of cap 700.

In some embodiments, each sub-set of cords 604, 606, 608 and 610 may first be connected to each other to form a bundle and may then be connected to cap 700.

As illustrated in FIG. 7B, a prosthesis mitral valve 600 may comprise flexible asymmetrical ring 601 attached to two leaflets (e.g., leaflets 602A and 602P). In some embodiments, each of the two leaflets may have attached a set of cords, e.g., sub-sets cords 604 (not shown), 606 (not shown), 608 and 610. In some embodiments, each set of cords per each of the two leaflets may be attached to a single cap 700, whereas each cap 700 may connect the mitral valve prosthesis 600 to papillary muscles 720 of the heart, via connection of each sub-set of cords 610 to their respective cap 700.

As mentioned hereinabove, according to some embodiments, each sub-set of cords 604 (not shown), 606 (not shown), 608 and 610 may be made of the same piece of material as the material that anterior and posterior leaflets are made of. Such cords, which each may be considered as an extension of leaflets 602A and 602P, may be referred to as primary cords. According to some embodiments, further cords may be attached to both the anterior leaflet 602A and posterior leaflet 602P. Each of these secondary cords may be made from a different and separate piece of material from that used to construct the leaflets and primary cords. The secondary cords may be configured to connect the bottom side of each of leaflets 602A and 602P to a point along a primary cord. The point of connection of a secondary cord along a primary cord may be the middle of the primary cord, though other locations along the primary cord may be implemented as points of connection so as to achieve better coaptation of the leaflets. A secondary cord may typically be sutured on one of its ends to the anterior leaflet 602A or posterior leaflet 602P and on its other end, the secondary cord may be sutured to the primary cord. When attaching, e.g., via sutures, a secondary cord to the anterior or posterior leaflets 602A or 602P, respectively, one should avoid injury of the outer surface of anterior leaflet 602A or of posterior leaflet 602P outer surface, in order to prevent clotting along the attachment line, e.g., suture line. For example, when using microscopic sutures, there is less chance of injuring either leaflets 602A and 602P. The purpose of the secondary cords is to provide additional support for the prosthetic valve against the pressure applied onto the ventricular side of the prosthetic valve during systole phase.

Figure 8A:
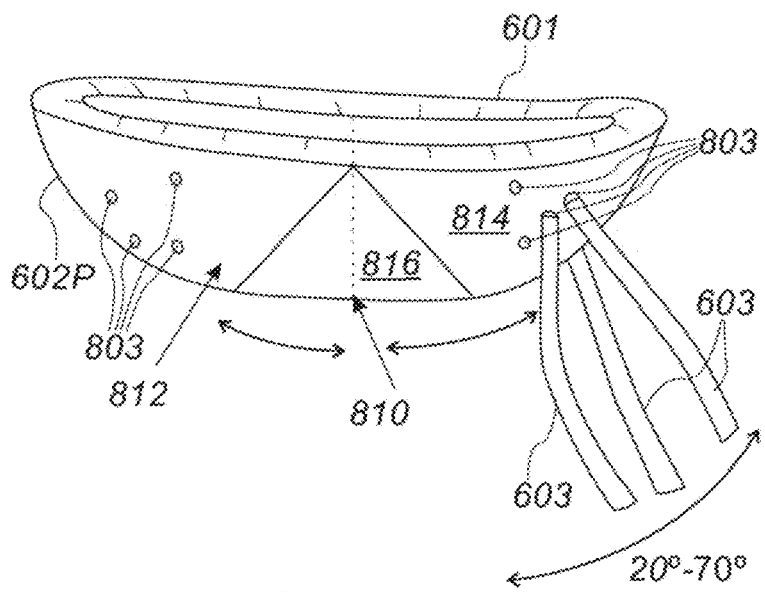
FIGS. 8A-8B are schematic illustrations of possible locations of the cords with respect to a leaflet, and a cross section of the cords when attached to the leaflet, respectively, in accordance with some embodiments of the disclosure.
Figure 8B:
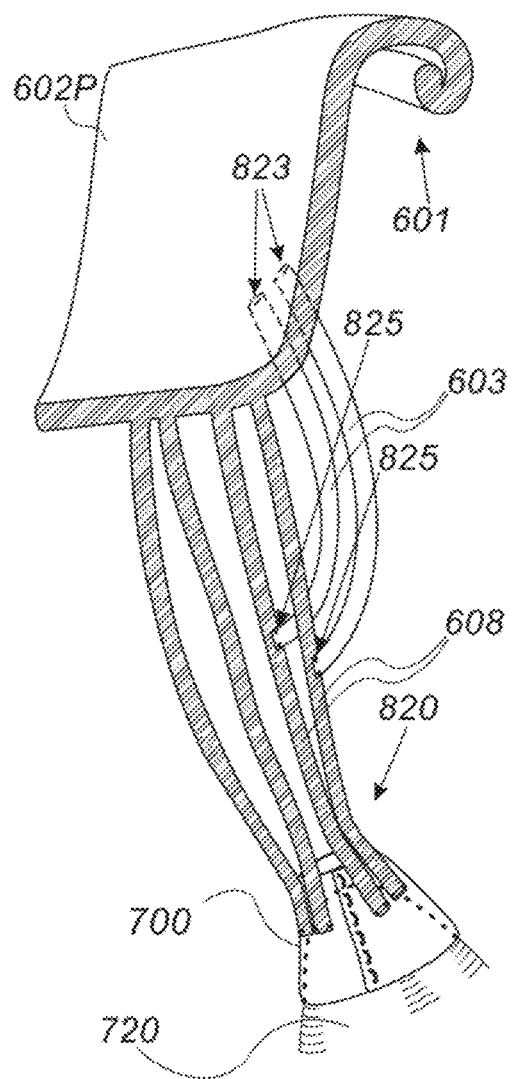

FIGS. 8A-8B are schematic illustrations of possible locations of secondary cords with respect to posterior leaflet, and a cross section of the primary and secondary cords when attached to the posterior leaflet, respectively, in accordance with some embodiments of the disclosure. As illustrated in FIG. 8A, posterior leaflet 602P may be rolled on its posterior end to form ring 601. In some embodiments, posterior mitral leaflet 602P may be divided into several areas. Areas 812 and 814 may be areas at which secondary cords, e.g., cords 603, may be connected to. However, there may be an area 816 along posterior leaflet 602P, which should be cords free, i.e., no secondary cords should be connected to area 816. This is due to the fact that area 816 is an area where high pressure is applied onto once posterior leaflet 602P is connected to the heart as part of a prosthetic valve during the ventricular systole. In some embodiments, area 816 may include approximately 2-5 mm to the right of the middle line 810 of posterior leaflet 602P, and approximately 2-5 mm to the left of the middle line 810 of posterior leaflet 602P. In some embodiments, area 816 may be 3 mm to the right and 3 mm to the left of the middle line 810 of posterior leaflet 602P. The secondary cords may be designed to assist in providing additional support to the posterior leaflet 602P when the pressure gradient is increased during the ventricular systole.

In some embodiments, the secondary cords 603 should not reach the ends of areas 812 and 814 of posterior leaflet 602P, when in laid out configuration. In some embodiments, no cords should be connected to the ends of areas 812 and 814, which are in close proximity to ring 601. For example, the cords may be located along either of areas 812 and 814 along approximately 20 degrees to 70 degrees of the entire posterior leaflet 602P layout, with respect to the middle line 810 of posterior leaflet 602P. Other than that, the areas of posterior leaflet 602P which are located between middle line 810 and about 15-20 degrees from either side of middle line 810 may remain free of secondary cords.

FIG. 8B schematically illustrates a cross section of the posterior mitral valve showing the primary and secondary cords when attached to posterior leaflet 602P. FIG. 8B illustrates primary cords 608, which are made of the same piece of material as the leaflets. Primary cords 608, which extend from posterior leaflet 602P on one of their ends are attached to cap 700 on their other end. In some embodiments, primary cords 608 may be connected to one another such to form a bundle (not shown), which may then be connected to the external side of cap 700. Cap 700 may then be connected to papillary muscles 720.

According to some embodiments, primary cords 608 may be connected to secondary cords 603, whereby each of the secondary cords 603 may be connected to posterior leaflet 602P on one end, e.g., end 823, and to a point of contact along a primary cord on the opposite end of each of the secondary cords 603, e.g., end 825. According to some embodiments, the secondary cords 603 should be around 30-40% thicker and wider compared with the primary cords 608. Depending on the desired prothesis, anywhere from one to four secondary cords can be used for each leaflet scallop of the posterior mitral leaflet (602P).

Figure 9A:
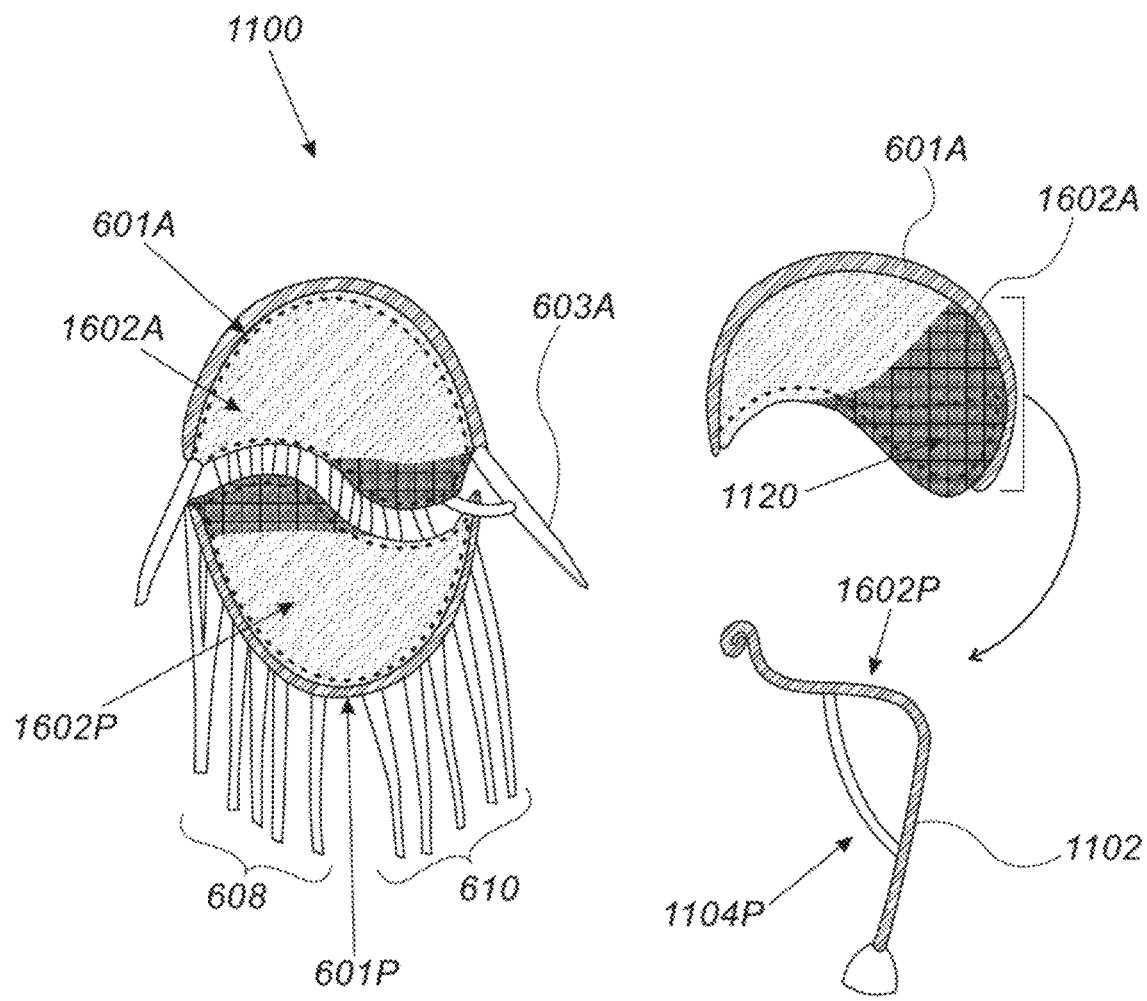
FIGS. 9A-9B are schematic illustrations of a prosthetic mitral valve having two leaflets attached, in an alternative design featuring a curved (ellipsoid/droplet) configuration, such to enlarge the coaptation surface, and a possible coaptation surface configuration, respectively, in accordance with some embodiments of the disclosure.
Figure 9B:
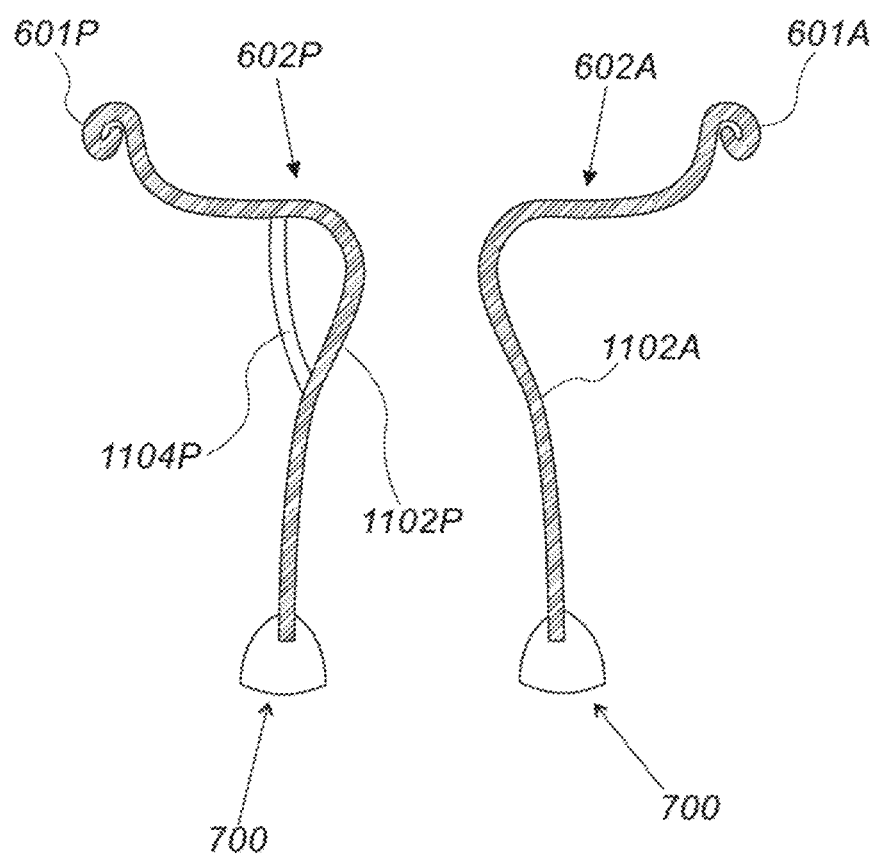

FIG. 9A-9B are schematic illustrations of a prosthetic mitral valve having two leaflets attached in an alternative design featuring a curved (ellipsoid/droplet) configuration, such to enlarge the coaptation surface, and a possible coaptation surface configuration, respectively, in accordance with some embodiments of the disclosure. According to FIG. 9A, a prosthetic mitral valve 1100 may comprise two leaflets, e.g., anterior leaflet 1602A and posterior leaflet 1602P, whereby each of the leaflets 1602A and 1602P may have a semi-circular shape and together these two leaflets may create the 'yin and yang' shape. In some embodiments, the leaflets shape may be designed in a semicircular fashion along half of the length of each leaflet such that both leaflets create an 'S' shaped seal when coapted.

This unique shape may enable sufficient coaptation between anterior leaflet 1602A and posterior leaflet 1602P, specifically at area 1120. In some embodiments, there may be coaptation or overlap between anterior leaflet 1602A and posterior leaflet 1602P along area 1120. Symmetrically, there may be a similar area of coaptation or overlap between posterior leaflet 1602P and anterior leaflet 1602A (not shown). Similarly, to valve 600 detailed hereinabove, each of the leaflets may comprise a respective ring, e.g., ring 601A and ring 601P, which may be formed by rolling onto itself an end of the material from which each of the leaflets is constructed.

According to FIG. 9B, in close proximity to the area of coaptation, there may be two configurations of coaptation between anterior leaflet 1602A to posterior leaflet 1602P. In some embodiments, as with respect to prosthetic valve 600, prosthetic valve 1100 may comprise two types of cords; primary cords and secondary cords. According to some embodiments, a primary cord may be constructed as an extension to either the anterior or posterior leaflets 1602A and 1602P, respectively. That is, a primary cord, e.g., primary cords 1102A and 1102P may be constructed from the same piece of material as the respective leaflet, anterior leaflet 1602A and posterior leaflet 1602P. Primary cords 1102A and/or 1102P may extend on one end from the mid-section of a respective leaflet and may be connected on the other end to a cap. According to some embodiments, secondary cords, e.g., cords 1104P, may be only attached onto the posterior leaflet 1602P. The secondary cords, e.g., cord 1104P may be connected on one end to the mid-section of the posterior leaflet 1602P, and on the other end to the mid-section of a primary cord 1102P. According to some embodiments, the secondary cords 1104P may be added in order to better mimic the native mitral valve, which includes additional shorter cords connecting between the posterior leaflet and the posterior primary cords. The addition of secondary cords may allow the posterior leaflet to withstand the pressure applied onto the posterior leaflet during systole phase, and to create appropriate coaptation (or closure) of the leaflets during systole phase of the heart cycle, and further to allow the leaflets to open during diastole phase.

For example, posterior leaflet 1602P may have attached a secondary cord 1104P on the posterior edge of leaflet 1602P. The secondary cord 1104P may further be connected to the mid-section of a primary cord 1102P.

In some embodiments, each bundle of cords and/or each cord may be attached to a cap, e.g., cap 700, which may connect the cords to the papillary muscles of the heart.

Figure 10:
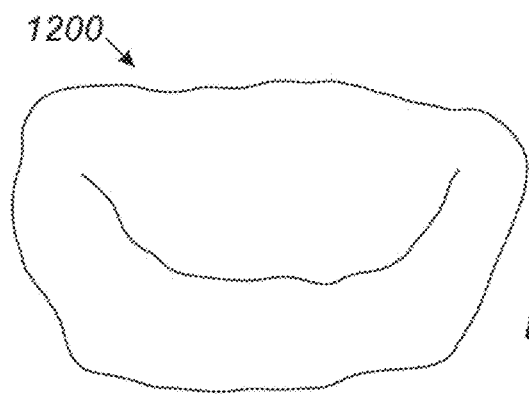
FIG. 10 is a schematic illustration of a measured copy of a patient's mitral valve, derived from a 2D or 3D echocardiographic image, in accordance with some embodiments of the disclosure.

FIG. 10 is a schematic illustration of a measured copy of a patient's mitral valve, in accordance with some embodiments of the disclosure. In some embodiments, measurements of length, width and heights of the leaflets section may be obtained via echocardiography, though other imaging methods may be used, e.g., cardiac CT, or cardiac MRI, and so on. Hence, the dimensions and shape of a prosthetic mitral valve 1200 may be substantially an exact copy of a patient's natural or native mitral valve.

Figure 11:
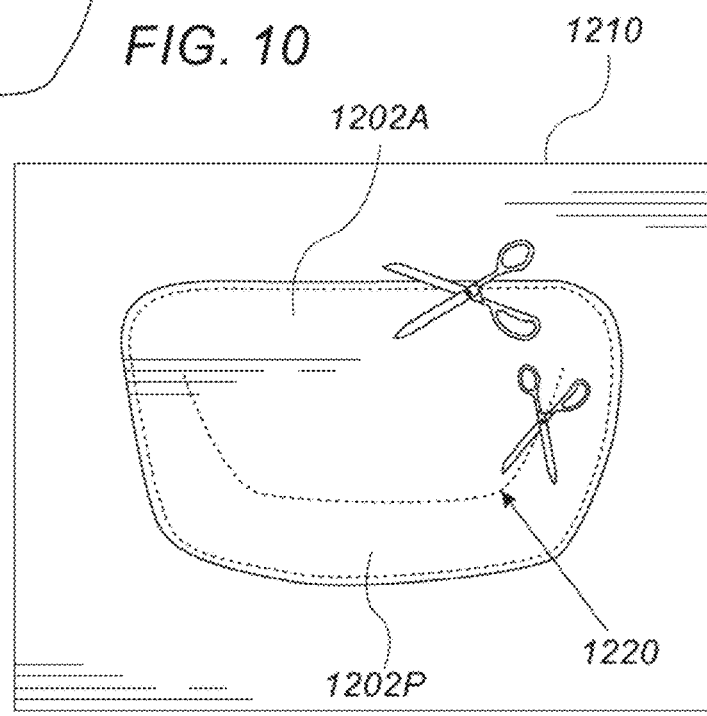
FIG. 11 is a schematic illustration of the forming of a two leaflet prosthesis, in accordance with some embodiments of the present disclosure.
Figure 12:
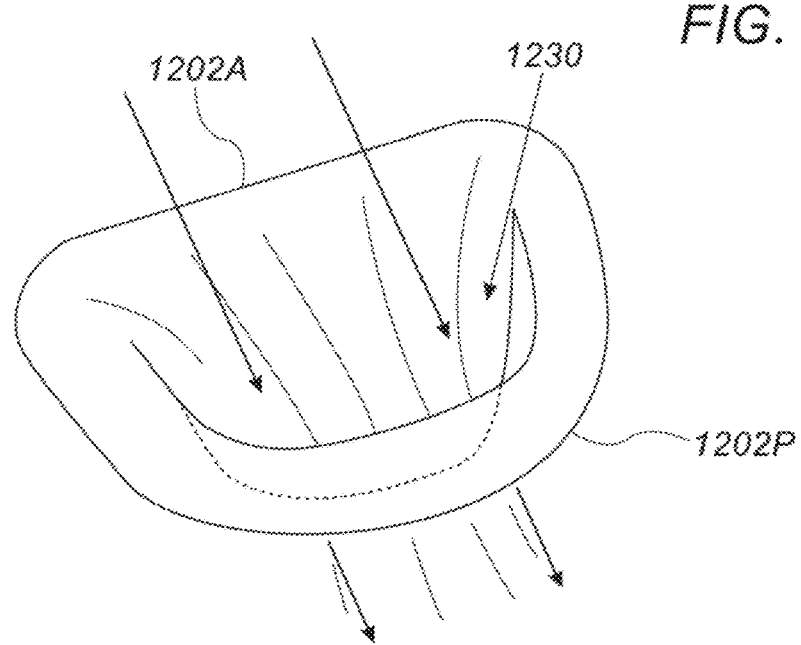
FIG. 12 is a schematic illustration of an opening formed along a leaflets section, in accordance with some embodiments of the disclosure.

FIG. 11 schematically illustrates the forming of a two-leaflet prosthesis, in accordance with some embodiments of the present disclosure. In some embodiments, the basis of the valve, i.e., the leaflets section may be cut out of a single piece of material 1210, based on the cross-sectional image of the heart of the intended recipient, as illustrated in FIG. 12. The size of the leaflets section may be cut in a way such to replicate the prosthesis image in a 1:1 scale, and an incision 1220 may be made along the middle of the leaflet section, in crescent or semicircular form, in order to provide for the opening 1230, and the definition of the two leaflets, e.g., anterior leaflet 1202A, and posterior leaflet 1202P, as illustrated in FIG. 12.

FIG. 12 schematically illustrates an opening formed along a leaflets section, in accordance with some embodiments of the disclosure. In some embodiments, an opening or orifice 1230 may be formed (e.g., cut) in single piece of material 1210, and two leaflets 1202A and 1202P may be formed on opposite sides of opening 1230. Once orifice 1230 is present by cutting through the single piece of material 1210, the two leaflets, e.g., anterior leaflet 1202A and posterior leaflet 1202P may be in the form of flaps that collapse into orifice 1230, thus further creating a single-directional flow of blood through orifice 1230, i.e., from the left atrium to the left ventricle of the heart.

Figure 13:
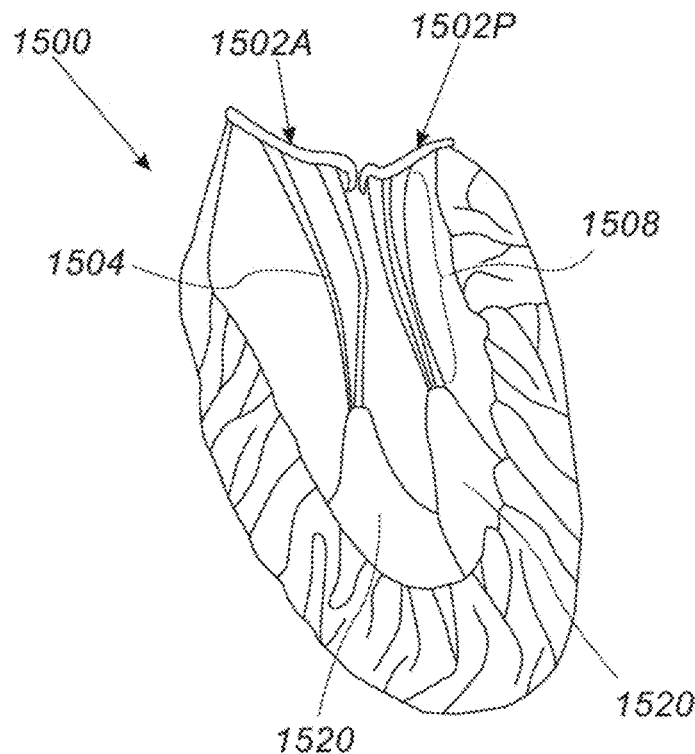
FIG. 13 is a schematic illustration of an echocardiography or MRI scan of a patient's left heart chamber or ventricle, in accordance with some embodiments of the disclosure.

FIG. 13 schematically illustrates an echocardiography or MRI scan of a patient's left heart chamber or ventricle, in accordance with some embodiments of the disclosure. In some embodiments, a patient's left ventricle 1500 may be imaged or scanned by echocardiography. CT or MRI, or other imaging techniques. Such an image or scan of the left ventricle 1500 may provide the exact or substantially exact length of the required patient's cords, from the tip of the papillary muscles 1520 to the valve leaflets 1502A and 1502P. This enables fabricating a customized prosthesis mitral valve per patient's anatomical and physiological requirements.

Figures 14A, 14B:
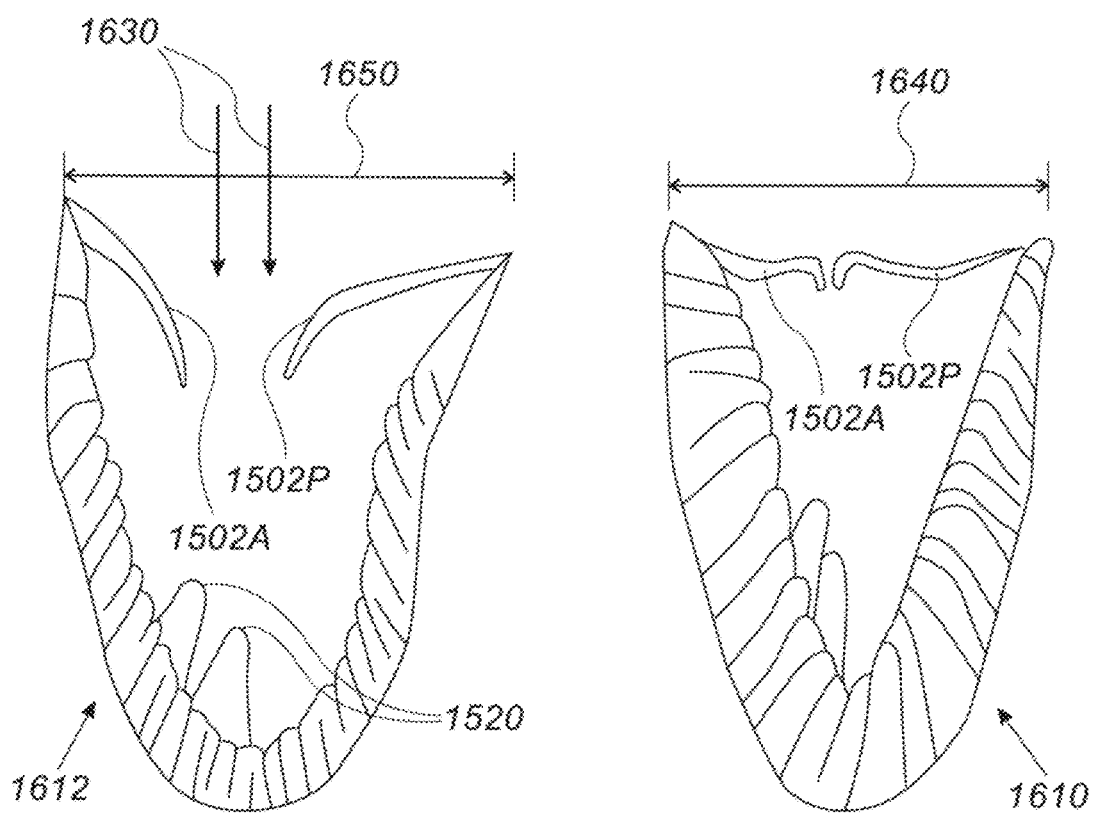
FIGS. 14A-14B are schematic illustrations of a patient's left ventricle during diastole and during systole, respectively, in accordance with some embodiments of the present disclosure.

FIGS. 14A-14B are schematic illustrations of a patient's left ventricle during diastole and during systole, respectively, in accordance with some embodiments of the present disclosure. In some embodiments, as illustrated in FIG. 14B, the left ventricle during systole phase, i.e., left ventricle 1610, may comprise a smaller annulus diameter 1640 compared to the annulus diameter 1650 of the left ventricle 1612 during diastole phase, illustrated in FIG. 14A. When blood flows into the left ventricle during diastole, left ventricle 1612 may become filled with blood, and thus the annulus diameter 1650 becomes large. After blood flows from the left ventricle to the patient's body blood system, such to reach the organs, blood leaves left ventricle 1610 during systole phase. Thus, the volume of left ventricle 1610 during systole is smaller compared to that of left ventricle 1612 during diastole, which causes annulus diameter 1640 during systole phase to be smaller compared to the annulus diameter 1650 during diastole.

Since the annulus and the leaflets 1502A and 1502P are required to enable flexibility when repeatedly changing their diameter and size during the reoccurring phases of the heart's function (i.e., systole and diastole), it should be clear that the annulus and leaflets are desired to be made of an elastic material, as the tissue that the natural mitral valve is made of. Accordingly, a prosthesis with no stents, no metal rings, and no rigid material is disclosed, and a certain amount of compliance and elasticity is required by the materials selected for manufacturing the leaflets 1502A and 1502P and the ring.

FIGS. 15A-15B are schematic illustrations of extensions attached to the anterior leaflet and to the posterior leaflet, respectively, in accordance with some embodiments of the disclosure. In some embodiments, as illustrated in FIG. 15A, the anterior leaflet 1202A may comprise an extension 1703 which comprises additional material to extend the size of anterior leaflet 1202A. The extension 1703 is dimensioned at about 1-5 mm in length and a width of substantially the incision made to form the anterior leaflet (e.g. incision 1220 of FIG. 11). In some embodiments, the extension 1703 is sutured on one end to the edge of the anterior leaflet 1202A (see incision 1220 of FIG. 11) and on the other end would comprise cords 1704 which may resemble cords 604, 606 of FIG. 6A.

As illustrated in FIG. 15B, the posterior leaflet 1202P may comprise an extension 1709 which comprises additional material to extend the size of anterior leaflet 1202P. The extension 1709 is dimensioned at about 1-5 mm in length and a width of substantially the incision made to form the anterior leaflet (e.g. incision 1220 of FIG. 11). In some embodiments, the extension 1709 is sutured on one end to the edge of the anterior leaflet 1202P (see incision 1220 of FIG. 11) and on the other end would comprise cords 1708 which may resemble cords 608, 610 of FIG. 6A.

As illustrated in FIG. 15B, the posterior leaflet 1202P has attached an extension 1709 on one end (the leaflet end) and cords 1708 on the other end. The cords 1708 are connected on one end to the extension 109 and on the other end to the cap 1870, which may resemble in structure the cap described in connection with FIG. 7A. The anterior leaflet 1202A has attached an extension 1703 on one end (the leaflet end) and cords 1704 on the other end. The cords 1704 are connected on one end to the extension 1703 and on the other end to the cap 1870, which may resemble in structure the cap described in connection with FIG. 7A.

Each of the cords 1704 and 1708 may comprise several cords also described herein as primary cords, e.g., four primary cords, though any other number of cords may be implemented depending on the specific requirements for each patient. In some embodiments, cords may also comprise secondary cords (not shown) as described herein above.

FIGS. 16A-16B are schematic illustrations of side-views of the mitral valve prosthesis with extensions and attached cords, during diastole and systole, respectively, in accordance with some embodiments of the disclosure. Referring now to FIG. 16A, a side view of the mitral valve prosthesis showing the profile of the mitral valve prosthesis when the heart is in the diastole and to FIG. 16B a side view of the mitral valve prosthesis when the heart is in diastole. Anterior leaflet 1202A and posterior leaflet 1202P, located at a distance from one another, in order to enable blood to flow through the orifice between leaflets 1202A and 1202P into the left ventricle, extensions 1703, 1709 enable the valve prosthesis to have an enhanced coaptation profile. Each of leaflets 1202A and 1202P may have attached extensions 1703, 1709 providing additional material to the anterior and posterior leaflets provide the necessary coaptation during systole so as to prevent backflow of blood into the atria and to provide support to the left ventricle during systole.

In some embodiments, extension 1703 and extension 1709 are prepared of different size (e.g. length, width and shape). In some embodiments, the cords 1704, 1708 may be bundled and secured together through suturing, prior to being attached to the cap 1870.

Extensions 1703 and 1709, respectively, which are configured to carry respective cords (1704, 1708), which are to resemble the cords of the native heart valve, and which are supposed to be inserted into the heart chamber and be attached onto the heart wall muscles or papillary muscles. For example, extension 1703 may carry cords or cords set 1704, while extension 1709 may carry cords or cords set 1708. Each of the at least two cords may be connected on another end (opposite the end connected to each of the extensions) to a cap 1870, which is configured to attach the valve to the papillary muscles.

In some embodiments, during diastole phase, as illustrated in FIG. 16A, the leaflets 1202A and 1202P, as well as the respective extensions 1703 and 1709 are located at a distance from one another, to enable blood flow in one direction, towards the left ventricle from the left atrium.

In some embodiments, during systole phase, as illustrated in FIG. 16B, the leaflets 1202A and 1202P, as well as their respective extensions 1703 and 1709 are located in close proximity to one another, to prohibit backflow or leakage of blood in the opposite direction, i.e., from the left ventricle to the left atrium. According to some embodiments, the extension, e.g., extensions 1703 and 1709 provide the necessary coaptation or closure of the valve in order to disable leakage of backflow of blood from the left ventricle to the eft atrium.

According to some embodiments, the extensions may be cut to fit the edges of the leaflet and measure a different width, of no less than 5 mm to ensure sufficient coaptation. The extensions are to be attached to the leaflet by being sutured, glued, stapled, or otherwise attached to the edges of the leaflets.

According to some embodiments, the cords, e.g., cords 1704 and 1708 may be individually attached, e.g., sutured, to the heart chamber wall or to the papillary muscle, or may be bundled together, e.g., in pairs, tetrads, and so on, depending on the design determined as optimal per the specific patient.

According to some embodiments, the cords may be asymmetric. That is, the cords may vary in size, as the left heart chamber has two papillary muscles, and the cords arising from various points of the leaflet extensions may comprise different length and distance from the top edge of those muscles. Thus, each cord or cord bundle may have an individualized, different length compared to the others. This will ensure perfect closure and sufficient coaptation length of the prosthesis valve.

In some embodiments, the cords, e.g., cords 1704 and 1708, which arise from the leaflet extensions, e.g., extensions 1703 and 1709, respectively, may be distributed along the edge of the anterior and posterior leaflet extensions, so as to distribute tension evenly along the margin of those leaflets, when the valve moves in-vivo, therefore reduce wear and tear of the prosthesis valve.

Figure 17:
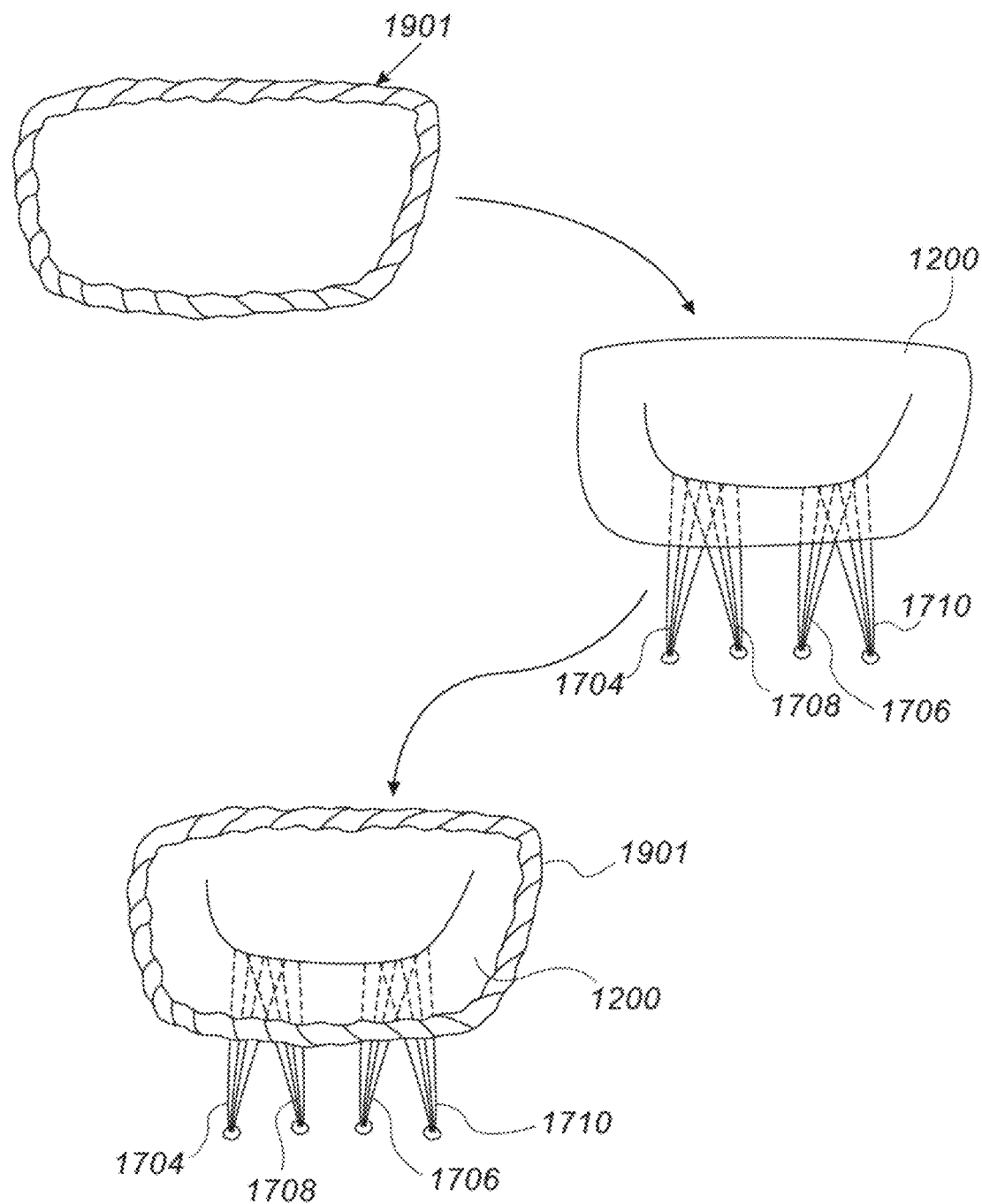
FIG. 17 is a schematic illustration of the attachment of an asymmetrical flexible ring onto the perimeter of the valve prosthesis to mimic the native annulus, in accordance with some embodiments of the disclosure.

FIG. 17 is a schematic illustration of the attachment of an asymmetrical flexible ring onto the perimeter of the valve prosthesis to mimic the native annulus, in accordance with some embodiments of the disclosure. According to some embodiments, a flexible ring 1901 may be formed by rolling a piece of elongated material onto itself and closing it into a ring shape, or by rolling a piece of material with a hole in the middle onto itself, towards the outside of the material. In some embodiments, the rolled ring 1901 may be attached to the perimeter of the mitral valve prosthesis 1200 to allow surgical attachment, e.g., suturing to the patient's annulus, to allow better stiffness of the annulus, and in case an elastic material is used to provide better elasticity during the heart cycle of changing between systole and diastole. The rolled ring 1901 may fit the perimeter of the initially cut valve 1200 (FIG. 10).

According to some embodiments, the outer ring reinforcement 1901 may be made of an elastic material comprising variable elasticity, to allow for variable dilation and contraction of the prosthesis valve during the heart cycle of diastole and systole, respectively. In some embodiments, the elasticity of ring 1901 may be derived from continuous study of the movement of the patient's native annulus based on 3D echocardiography studies.

In some embodiments, the reinforcement ring 19010 may be exposed to the blood environment inside the heart, or may be rolled into a sandwich engulfing the elastic material, which may be made from the same material as the leaflets surrounding it.

As illustrated in FIG. 17, the prosthesis valve 1200 may comprise cords 1704 and 1706, which may be attached to anterior leaflet 1202A (via or without extensions), and cords 1708 and 1710, which may be attached to posterior leaflet 1202P (via or without extensions). As illustrated in FIGS. 16A-16B, the cords may be attached to at least two caps configured to attach the valve 1200 to the papillary muscles of the heart, thus enable a suitable attachment of the mitral prosthesis valve 1200 to the left ventricle of a patient, per the specific anatomical and physiological requirements of the specific patient.

Figure 18A:
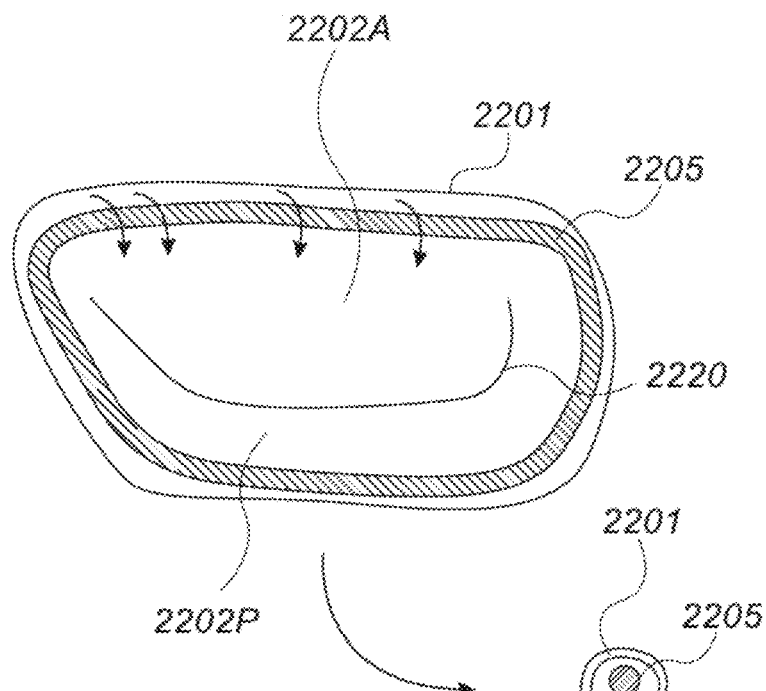
FIGS. 18A-18B are schematic illustrations of an elastic material to be inserted into the rolled valve ring, before and after the ring is rolled over it, respectively, in accordance with some embodiments of the disclosure.
Figure 18B:
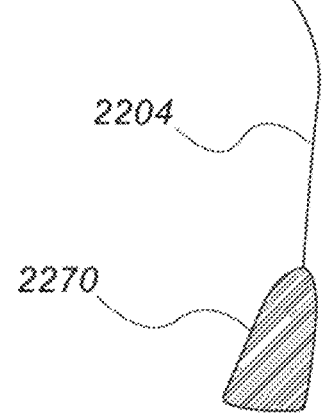

FIGS. 18A-18B are schematic illustrations of an elastic material to be inserted into the rolled valve ring before and after the ring is rolled over it, respectively, in accordance with some embodiments of the disclosure. According to some embodiments, as illustrated in FIGS. 18A-18B, a valve ring 2201 may comprise the addition of an elastic material 2205, which may be inserted within ring 2201 such that ring 2201 is rolled over elastic material 2205, and elastic material 2205 is "sandwiched" within ring 2201. The addition of elastic material 2205 within ring 2201 is for providing extra elasticity to ring 2201, which may assist in better mimicking the elastic character of a natural mitral valve. In some embodiments, elastic material 2205 may be rubber or any other biocompatible synthetic material. In some embodiments, the shape of elastic material 2205 is similar to the shape of ring 2201 into which it is inserted, in order to enable an easy insertion of elastic material 2205 into ring 2201.

According to some embodiments, and as illustrated in FIG. 18B, ring 2201 (which may be made of the same material as the leaflets or may be made from an alternative material extension attached to the outer rims of the leaflets) may be rolled over elastic material 2205, towards the inner side of the synthetic valve. e.g., toward incision 2220, which may be made along the middle of the leaflet section, in crescent or semicircular form, in order to provide for an opening between the two leaflets defined by incision 2220, e.g., anterior leaflet 2202A, and posterior leaflet 2202P. Incision 2220 is in fact the actual mitral valve prosthesis orifice through which blood flows from the left atrium to the left ventricle. Accordingly, the outer margins of the mitral valve prosthesis may comprise ring 2201, then connected to ring 2201 is the main surface of the leaflets, e.g., leaflets 2201A and 2202P, which are then connected to the papillary muscles through cap 2270 via cords, e.g., cord 2204.

Figure 19:
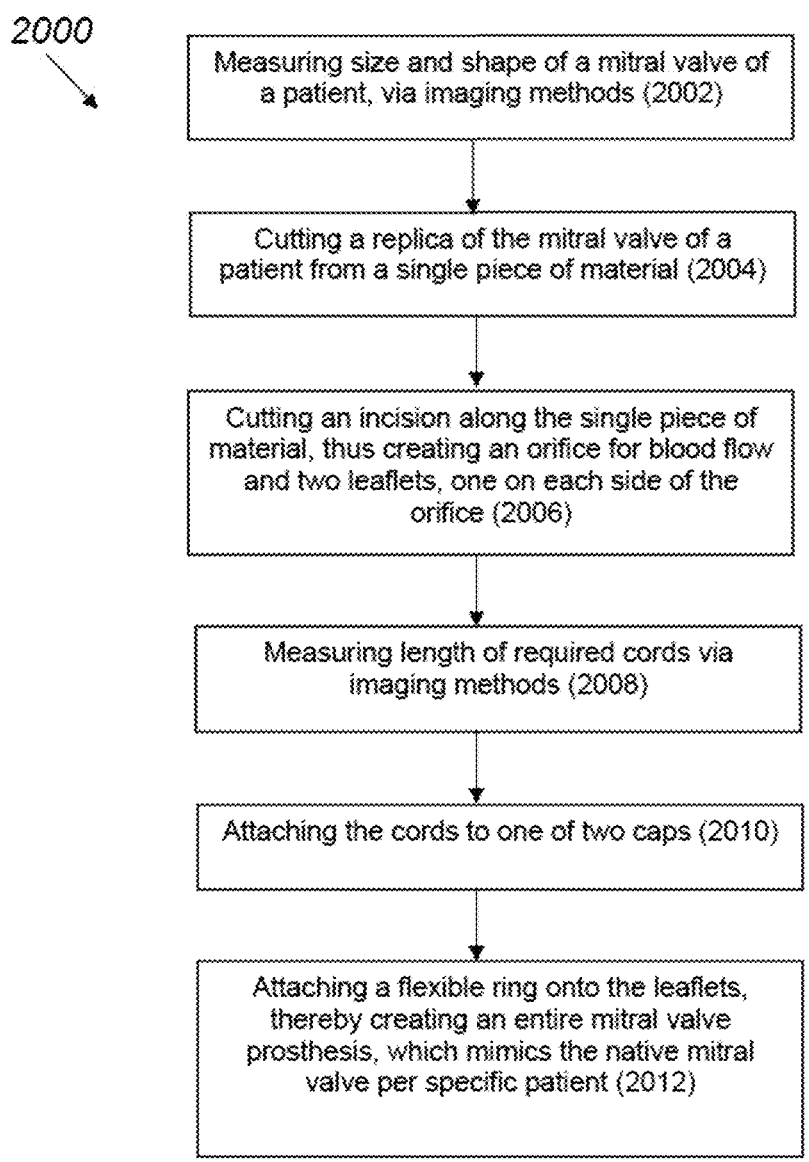
FIG. 19 is a schematic flow chart illustrating a method for fabricating a mitral valve prosthesis, in accordance with some embodiments of the disclosure.

FIG. 19 is a schematic flow chart illustrating a method for fabricating a mitral valve prosthesis, in accordance with some embodiments of the disclosure. According to some embodiments, method 2000 for fabricating a mitral valve prosthesis customized per patient, may comprise operation 2002, which may comprise measuring size and shape of a mitral valve of a patient, via imaging methods. Imaging methods by which the shape and size of a specific patient's mitral valve is measured, may be echocardiography, cardiac CT, cardiac MRI, and any other imaging method. Method 2000 may further comprise operation 2004 of cutting a replica of the mitral valve of a patient from a single piece of material, in a 1:1 scale. In some embodiments, method 2000 may comprise operation 2006 of cutting an incision along the single piece of material thus creating an orifice for blood flow and creating two leaflets, one on each side of the orifice. Method 2000 may comprise operation 2008 of measuring length of required cords via imaging methods, which may be similar to the imaging methods of measuring the shape and size of the mitral valve, as in operation 2002.

In some embodiments, method 2000 may further comprise operation 2010 of attaching the cords to one of two caps, which are configured to attach the cords to the papillary muscles of the heart.

In some embodiments, method 2000 may comprise operation 2012, which may comprise attaching a flexible ring onto the leaflets, thereby creating the entire mitral valve prosthesis, which mimics the native mitral valve per specific patient.

In some embodiments, method 2000 may further comprise an optional operation, which may comprise attaching extensions to each of the two leaflets to carry the cords, as measured in operation 2008. These extensions may assist in providing proper coaptation and closure during systole phase of the heart cycle.

According to embodiments of the present disclosure, the motivation of implementing a method for manufacturing a personalized naturally designed mitral valve prosthesis is in the expectation that the valve will last longer than current valve prostheses, since the personalized valve is manufactured such to fit the exact anatomical dimensions and limitations of each patient. An individualized prosthesis will serve better than any of the best quality available prosthesis, because it is made to fit for the patient, permitting superior hemodynamic performance and faster or better heart recovery after implementation of the prosthesis.

Figure 20A:
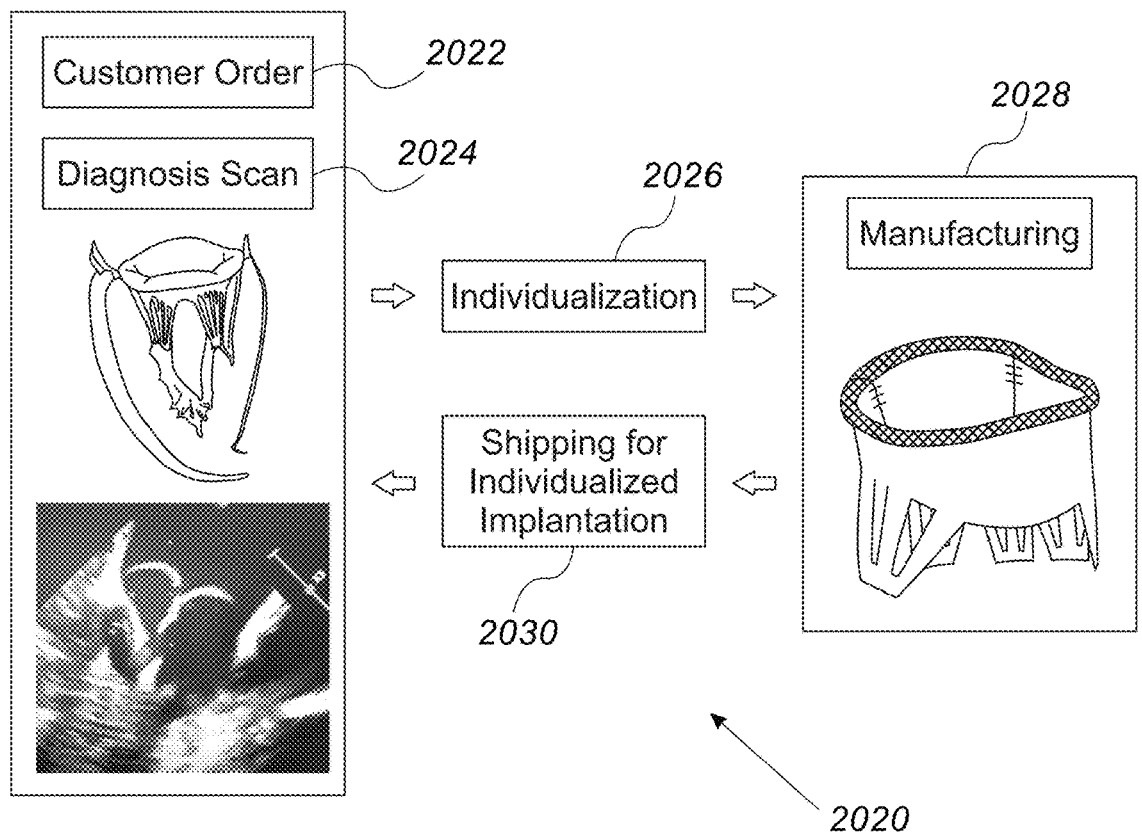
FIG. 20A is a schematic diagram illustrating a method for manufacturing a personalized mitral valve prosthesis, in accordance with some embodiments of the disclosure.

Reference is made to FIG. 20A, which is a schematic diagram illustrating a method 2020 for manufacturing a personalized mitral valve prosthesis, in accordance with some embodiments of the disclosure. According to method 2020, the valve prosthesis is not an off-the-shelf product as in current practice. Instead after ordering a personalized mitral valve prosthesis in operation 2022, remote diagnosis imaging scans performed in operation 2024, may be used as basis to individualizing the mitral valve prosthesis dimensions in operation 2026, to manufacture accordingly a more accurate personalized valve prosthesis for an individual patient in operation 2028. In some embodiments, method 2020 may comprise packaging and shipping the personalized naturally designed mitral valve prosthesis for implantation into the specific patient, in operation 2030. In some embodiments, the scans are made very short time prior to manufacturing 2028 so as to enable the personalized mitral valve prosthesis to be fully compatible with the patient.

Figure 20B:
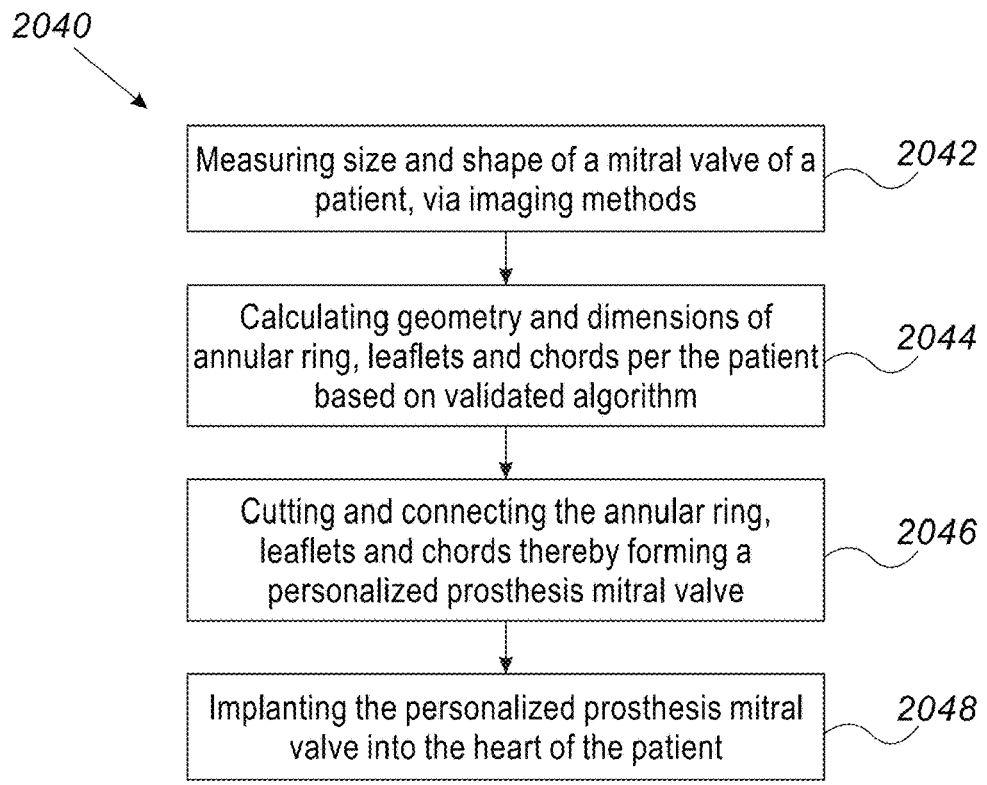
FIG. 20B is a schematic flow chart illustrating a method for manufacturing a personalized mitral valve prosthesis, in accordance with some embodiments of the disclosure.

Reference is now made to FIG. 20B, which is a schematic flow chart illustrating a method 2040 for manufacturing a personalized mitral valve prosthesis, in accordance with some embodiments of the disclosure. Method 2040 is similar to method 2020, though may include different operations. In some embodiments, method 2040 may comprise operation 2042, which may comprise measuring size and shape of a native mitral valve of a patient, via imaging methods. The diagnosis imaging techniques may be but are not limited to current imaging techniques including 2D and 3D echocardiography, computed tomography (CT) or Cardiac magnetic resonance (CMR).

In some embodiments, method 2040 may further comprise operation 2044, which may comprise calculating geometry and dimensions of annular ring, leaflets and chords of the mitral valve prosthesis per the specific patient based on validated algorithms. The validated algorithms, e.g., calculations that assist in defining the dimensions of a mitral valve prosthesis that suits each specific patient will be detailed hereinbelow.

In some embodiments, method 2040 may comprise operation 2046, which may comprise cutting and connecting, based on the calculations, all parts of a personalized prosthesis mitral valve, i.e., the annular ring, leaflets and chords, which may be done per each patient, per the patient's specific anatomy and personal physiology, thereby forming a personalized mitral valve prosthesis.

In some embodiments, method 2040 may comprise operation 2048, which may comprise implanting the personalized prosthesis mitral valve into the heart of the patient for which the personalized mitral valve prosthesis has been manufactured.

Reference is now made to FIGS. 21A-21B, which illustrate a schematic illustration of a ring-shaped valvular edge preserved when removing the native mitral valve in clinical practice, and a schematic illustration of an ellipse shape annulus model with AL-PM diameter as major axis and A-P diameter as minor axis used to calculate annular circumference (AC) of the valve prosthesis, respectively. In accordance with some embodiments of the disclosure.

In some embodiments, the following abbreviations are used with respect to Mitral Valve Prosthesis Annulus components:
Mitral annulus (MA);
Annular circumference (AC);
Anterior-posterior diameter (A-P);
Anterolateral posteromedial diameter (AL-PM):
Commissural diameter (C-C); and
Annular area (AA).

Mitral Valve Prosthesis Annulus:

According to some embodiments, the personalized mitral valve prosthesis of the present disclosure comprises a flexible annular ring dimensioned to match the native mitral annulus of a patient. According to the present disclosure, the mitral valve prosthesis may be individualized or personalized based on the following characteristics.

The first characteristic is that the annular ring of the prosthesis is manufactured without constraint from any rigid frame and is thus compliant with the patient's mitral annulus.

The second characteristic is that the dimensions of the prosthesis annular ring in terms of circumference are individualized based on the specific patient's diagnosis imaging result, e.g., as performed in operation 2022 of FIG. 20B. In some embodiments, the dimensions of the prosthesis annular ring are calculated as a function of anterior-posterior diameter (A-P) illustrated in FIG. 21A and anterolateral posteromedial diameter (AL-PM) illustrated in FIG. 21A when the mitral valve closes during left ventricular systole.

The third characteristic is that a ring-shaped valvular edge is preserved when removing the native mitral valve in clinical practice (FIG. 21A), and the annular ring of the prosthesis is to be stitched onto the native valvular edge; in other words, onto the necking down native annulus. The annular ring dimension of the personalized prosthesis in terms of annular circumference (AC) may be calculated according to equation (i):

$$AC = f(A\text{-}P \text{ diameter}, AL\text{-}PM \text{ diameter}, d) \quad \text{(i)}$$

whereby
A-P diameter is anterior-posterior diameter;
AL-PM diameter is anterolateral posteromedial diameter; and
d is the width of the annular ring's edge.

An approximate formula derived from an ellipse shape annulus with AL-PM diameter as major axis and A-P diameter as minor axis (FIG. 21B) is used to calculate AC(1) of the valve prosthesis based on equation (ii):

$$AC(1) = 2\pi \frac{A\text{-}P \text{ diameter-}2d}{2} + 4\left(\frac{AL\text{-}PM \text{ diameter-}2d}{2} - \frac{A\text{-}P \text{ diameter-}2d}{2}\right) \quad \text{(ii)}$$

In some embodiments, the annular ring circumference (AC) of the mitral valve prosthesis is required for further adjustment compared to the patient's native annulus, and such adjustment typically refers to reduction of the size of the annular ring circumference (AC). Under these circumstances, the annular ring of the mitral valve prosthesis may serve as annuloplastic treatment of a dilated annulus in some patients that suffer from such problem. In one aspect, the ratio of AC reduction may range from 0% to 20% and the actual value may be determined preferably by existing clinical diagnosis, or by mathematic model established by big data analysis or to be simply and more realistically determined based on a comparison with values indexed to body surface area (BSA) of healthy population. In another aspect, the AC reduction is also required by the tendency of annulus remodeling after prosthesis implantation when the leaflets coaptation is improved by the new valve prosthesis; thus, the ratio (λ) of reduction is also dependent on the potential of recovery of the patient's heart. In conclusion, AC (2) of the mitral valve prosthesis, which is the more accurate value of the annular circumference of the personalized mitral valve prosthesis may be calculated according to equation (iii):

$$AC(2) = \left[2\pi \frac{A\text{-}P \text{ diameter-}2d}{2} + 4\left(\frac{AL\text{-}PM \text{ diameter-}2d}{2} - \frac{A\text{-}P \text{ diameter-}2d}{2}\right)\right] \times (1 - \lambda) \quad \text{(iii)}$$

whereby λ is the ratio of AC reduction (from native annular ring circumference to annular ring of the personalized prosthesis).

According to some embodiments, an annular plication technique may be used when AC reduction is required. The annular plication may be a uniform annular plication along the annulus instead of localized annular plication, which is normally practiced during annuloplasty. Annular plication according to embodiments of the present disclosure may be more focused on posterior leaflet annulus due to the fact that the posterior leaflet makes up for the larger portion of the entire mitral valve circumference. In addition, the posterior annulus of a human heart lacks a fibrous skeleton, which causes it to be prone to dilatation, symmetric or asymmetric, and the posterior annulus could expand and cause leaflet distancing and leakage.

The fourth characteristic may be based on the fact that the mitral valve prosthesis according to the present disclosure refers to a prosthetic valve comprising two leaflets made up of an anterior leaflet 2210 (FIG. 22A) and a posterior leaflet 2220 (FIG. 22B). Accordingly, the annular ring of the valve prosthesis may also comprise two parts: an anterior leaflet annulus and a posterior leaflet annulus. The top edges of the anterior leaflet and the posterior leaflet may be jointed together following the direction of anterolateral to anterolateral and posteromedial to posteromedial to form the annular ring 2230 of the mitral valve prosthesis (FIG. 22C). That is, anterolateral side of anterior leaflet 2210 is attached to the anterolateral side of the posterior leaflet 2220, and the posteromedial side of the anterior leaflet 2210 is attached to the posteromedial side of the posterior leaflet 2220.

Annular ring 2230 may have a reinforced structure and is made up of multi-layered leaflet material. The height of annular ring 2230 may range from 1 mm to 4 mm and more preferably may range between 2 mm to 3 mm which may allow the clinical surgeon to stitch the valve annulus to the mitral annulus of the patient's heart. The number of layers may be two to four by folding or overlapping the top edges of the anterior leaflet and posterior leaflet onto themselves. In some embodiments, the annular ring may comprise surgical sutures 2316 for annular ring reinforcement.

The mitral valve prosthesis of the present disclosure may have an asymmetrical annular ring formed from a combination of the anterior leaflet annulus and posterior leaflet annulus which are the reinforced top edges of the leaflets. An example of such asymmetrical annular ring is shown in FIG. 22A and FIG. 22B, where the anterior leaflet annular circumference (AAC) 2212 is smaller than the posterior leaflet annular circumference (PAC) 2222, and the ratio (R) of AAC/PAC may range from 49/51 to 30/70, more preferably from 35/65 to 42/58. The anterior leaflet annular circumference (AAC) 2212 and the posterior leaflet annular circumference (PAC) 2222 may be calculated according to equations (iv) and (v), respectively:

$$AAC = AC \times \frac{R}{1+R} \quad \text{(iv)}$$

$$PAC = AC \times \frac{1}{1+R} \quad \text{(v)}$$

Figure 24A:
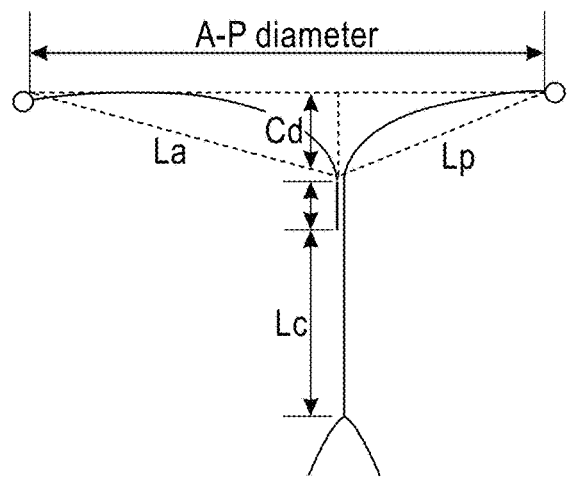
FIG. 24A is a schematic illustration of the relationship of multiple parameters that influence each other when leaflets of the prosthesis coapt, in accordance with some embodiments of the disclosure.

Mitral Valve Prosthesis Leaflets:

Reference is now made to FIG. 24A, which is a schematic illustration of the relationship of multiple parameters that influence each other when leaflets of the prosthesis coapt, in accordance with some embodiments of the disclosure, and to FIGS. 24B-24C, which are schematic illustrations of side view and perspective view, respectively, of coaptation of mitral valve leaflet, in accordance with some embodiments of the disclosure. According to some embodiments, the mitral valve prosthesis of the present disclosure may comprise two flexible, membrane-like leaflets which are suspended from the asymmetrical annular ring 2230. The two leaflets open during the diastole cycle to allow the blood to flow from the left atrium to the left ventricle and then the two leaflets close tightly so that the blood flow through the heart is in one direction without backflow through the valve during systole cycle. The dimension of the two leaflets is crucial to ensure the prosthesis valves open and close properly.

For a healthy mitral valve, a valve prosthesis can be tailored with its leaflet length duplicated from the diagnosis imaging results. However, for a patient whose mitral valve malfunctions and needs to be replaced, measurement of anterior leaflet length (La) and posterior leaflet length (Lp) is neither feasible nor useful in individualizing or personalizing a new valve prosthesis. Instead, the anterior-posterior diameter (A-P, which may be referred to A2P2) may be used as a reference to represent the minimum distance or length for leaflet coaptation. The ratio (r) of anterior leaflet length to posterior leaflet length may vary from 1/1 to 2/1 (which are reference ratios).

In some embodiments, in addition to the anterior-posterior diameter (A-P) and the ratio (r), the leaflet length is also affected by the coaptation depth (Cd), coaptation height (Coapt H) and the chord length (Lc). Accordingly, the anterior leaflet length (AL) and posterior leaflet length (PL) may be a function of all of the abovementioned parameters, as expressed by equations (vi) and (vii):

$$AL = f(A-P \text{ diameter}, r, Cd, Ch, Lc) \qquad (vi)$$

$$PL = f(A-P \text{ diameter}, r, Cd, Ch, Lc) \qquad (vii)$$

According to some embodiments, empirical formulas are used in calculating the anterior leaflet length (AL) and posterior leaflet length (PL) for animal models when anterior-posterior diameter (A-P) is less than 28 mm. These formulas proved to work in either pig or sheep models showing low mean trans-mitral pressure gradient and accepted leaflet coaptation (FIG. 24). The formulas (viii) and (ix) are as follows:

$$AL = (A-P \text{ diameter}) \div 2 + 10 \text{ (In millimetre)} \qquad (viii)$$

$$PL = (A-P \text{ diameter}) \div 2 + 5 \text{ (In millimetre)} \qquad (ix)$$

In some embodiments, the top edges of the anterior leaflet and posterior leaflet form the multi-layered reinforced annular ring, e.g., asymmetrical annular ring 2230, of the valve prosthesis. The top edge of the leaflets may be either straight or curved, i.e. semi-elliptical so that the finished valve prosthesis fits more accurately to the natural geometry of the left ventricle. Downward from the annular ring, two commissures form when the two leaflets join together, e.g., commissures 2310 and 2312 (FIG. 22C). The commissures incline inward and give a slight cone shape to the body of the valve prosthesis which fits better in the left ventricle for the shape and contour. The inclined angle ($\delta_0$) may range between 5 degrees to 20 degrees. The cone angle ($\delta_1$) is determined by the inclined angle ($\delta_0$) of the commissure edge of leaflets according to equation (x):

$$\delta 1 = \arctan\left[\frac{2\sin(\delta_0)}{\pi\cos(\delta_0)}\right]. \qquad (x)$$

According to some embodiments, the inclined angles ($\delta_0$) are equal for both leaflets, and thus the cone angle ($\delta_1$) is equal for both leaflets.

According to some embodiments, another element of a prosthesis leaflet that should be individualized or personalized is the free edges. The edge to edge coaptation between the anterior leaflet and posterior leaflet controls the function and performance of the prosthesis valve. Geometrically the leaflet free edge of the current invention is semi-elliptical. The length of the free edge may be calculated according to equation (xi):

$$\text{Length of free edge} = \{2\pi \times |AL(\text{or } PL) - b - CH \times \cos(\delta 0) - \text{Coapt } H| + 4[a - CH \times \sin(\delta 0) - |AL(\text{or } PL) - b - CH \times \cos(\delta 0) - \text{Coapt } H|]\} \div 2 \qquad (xi)$$

whereby CH denotes the length of the commissure edges 2214 and 2216 as shown in FIGS. 22A and 22B, respectively.

Figure 23A:
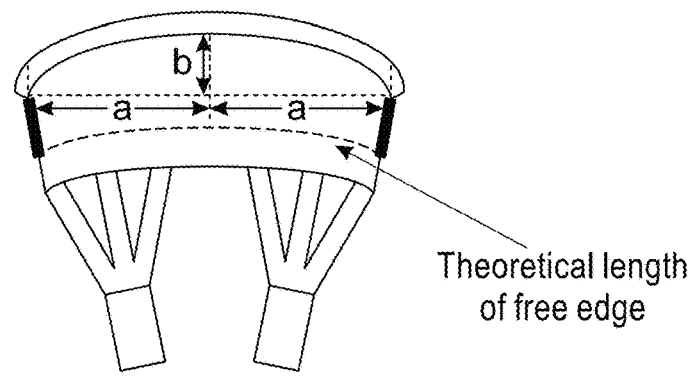
FIGS. 23A-23B are schematic illustrations of two examples of leaflets, either anterior or posterior, illustrating the theoretical length of the free edge of the leaflet, in accordance with some embodiments of the disclosure.
Figure 23B:
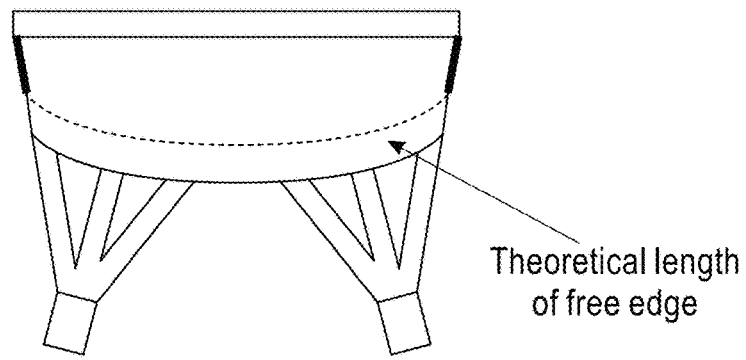

Parameters "a" and "b" are geometric parameters required to define and form the shape of the top edge of the anterior leaflet or posterior leaflet which is either curved as semi-ellipse with long axis of "a" and short axis of "b" as illustrated in FIG. 23A, or as a straight line as illustrated in FIG. 23B.

FIG. 23B is an extreme example in which the top edge of the leaflet is a straight line with "a=½ AAC (PAC)" and "b=0", the free edge of the leaflet may be calculated according to equation (xi) as:

$$\text{Length of free edge} = \{2\pi \times (AL(\text{or } PL) - CH \times \cos(\delta 0) - \text{Coapt } H) + 4[½(\text{or } PAC) - CH \times \sin(\delta 0) - (AL(\text{or } PL) - CH \times \cos(\delta 0) - \text{Coapt } H)]\} \div 2$$

Mitral Valve Prosthesis Chords:

In a normal mitral valve, the chords are fan-shaped running from the papillary muscles and being inserted into the leaflets. They are divided into primary, secondary and tertiary chords depending on where they attach.

The mitral valve prosthesis of the present disclosure merely comprises primary chords attached to the free edge of the anterior leaflet or posterior leaflet. Two sets of chords (FIG. 24B) and three chords (FIG. 24C) in each set are uniformly distributed along ⅜ of the free edge from each end; they are the anterolateral chords and posteromedial chords.

The chords play an important role to ensure an appropriate opening and closing of the valve prosthesis. Compared with the other geometrical characteristics of mitral valve, chords, specifically the length of chords are currently not well studied during clinical pre-diagnosis, especially per valve replacement. The chords measurement may be defined as the distance from the apex of the papillary muscle to the annulus plane, the distance from the apex of papillary muscle to the coaptation edge or the distance from the apex of the papillary muscle to the annulus.

In order to personalize the prosthesis chord length, the leaflet length (AL or PL), the leaflet coaptation height (Coapt H), the leaflet coaptation depth (Cd) and the distance from the apex of the papillary muscle to the leaflet coaptation edge (Lc) need to be correlated to ensure the function of the complex structured prosthesis. Thus, the length of the anterolateral chords (ACL) and the length of posteromedial chords (PCL) may be expressed as a function of multiple parameters according to equations (xii) and (xiii) below:

$$ACL = f(AL, \text{Coapt } H, Cd, Lc(\text{anterolatertal})) \qquad (xii)$$

$$PCL = f(AL, \text{Coapt } H, Cd, Lc(\text{posteromedlal})) \qquad (xiii)$$

A simplified method by using the measured distance from the apex of papillary muscle to the coaptation edge as the prosthesis chord length, i.e. ACL=Lc(anterolaterlal) and PCL=Lc(posteromedlal) is also introduced in the present disclosure; from design level, the three chords of each set will be merged at the free end and fused into a pledget like chord cap 2240 (FIG. 22A and FIG. 22B). A clinical surgeon may complete the last part of personalization of the mitral valve prosthesis by performing the on-site measurement and adjustment.

The personalized geometry and dimensions discussed hereinabove may be taken as inputs for various engineering drawing software or drawing tools.

The drawing may be printed out as a template for manually cutting the leaflets of the valve prosthesis, e.g., hand cut under a microscope.

The drawing may be progmnmned into a machining tool for example, a laser cutting machine for cutting the leaflets even more precisely and more efficiently compared to manual cutting.

The drawing may also be programmed into machining tools to make a personalized mold cutter or die cutter to be used for leaflet cutting at a lower temperature than the temperature at which laser cutting takes place, in order to minimize the thermal effect on the material that is cut for the valve prosthesis.

The mitral valve prosthesis may be created by joining the annulus and commissure edges of the anterior leaflet and posterior leaflet together following the direction of anterolateral to anterolateral and posteromedial to posteromedial (FIG. 22C). One way to join the two leaflets together may be by stitching with surgical suture, e.g., stitches 2314 in FIG. 22C.

The aforementioned valve prosthesis may further be packed, labelled and sterilized before release for usage, i.e., implantation into the patient which the valve prosthesis was personally manufactured for.

For ease of operation, the aforementioned valve prosthesis may be assembled onto a valve holder before packaging.

The valve prosthesis of the present disclosure may be shipped or otherwise transferred as a complete product for individualised implantation for the specific patient.

According to some embodiments, any of the disclosed anterior and posterior leaflets, any ring, any cords (and any sub-set of cords), any cap, and/or any combination thereof may be produced from natural materials and may avoid the inclusion of foreign material, such as pledgets. Homograft material and/or composite material, including various combinations of homograft, xenograft and/or autograft material, may further be used to fabricate the flexible ring, leaflets, cords, and caps. The material which forms the valve ring and the leaflets may comprise, but is not limited to, human, bovine or porcine pericardium, decellularized bioprosthetic material, woven biodegradable polymers incorporated with cells, and extracellular materials. Biodegradable natural polymers may include, but are not limited to, tofibrin, collagen, chitosan, gelatin, hyaluronan, and similar materials thereof. A biodegradable synthetic polymer scaffold that may be infiltrated with cells and extracellular matrix materials may include, but is not limited to, poly(L-lactide), polyglycolide, poly(lactic-co-glycolic acid), poly(caprolactone), polyorthoesters, poly(dioxanone), poly(anhydrides), poly(trimethylene carbonate), polyphosphazenes, and similar materials thereof. Flexible rings may further be customized to provide individualized flexibility or rigidity for the patient. Additionally, some components of the mitral valve prosthesis, including the cords, may be fashioned intraoperatively by autologous pericardium of the patient.

According to some embodiments, any of the disclosed asymmetrical flexible rings, which may comprise an anterior ring portion and a posterior ring portion, or which may be made as a single unit, may be formed by rolling or folding the edges of the leaflet(s) onto itself. In other embodiments, the flexible ring may further comprise at least two strands or layers of material, e.g., human, bovine or porcine pericardium, or any of the materials listed above, whereby the at least two strands or layers may be coiled, twisted, braided or looped one around the other. A ring structured in a coiled coil may comprise more strength compared to a ring formed by mere rolling of the edges of the leaflet onto itself, however, the coiled ring should maintain its elasticity.

According to some embodiments, the ring may comprise two strands or layers of material folded together to provide elasticity, with the addition of a third layer to provide structural stability. In some embodiments, the ring may comprise two layers made of bovine pericardium, while the third strand or layer may be made of Glycine or Proline in order to provide strength to the ring.

In some embodiments, the at least two layers or strands may be attached, e.g., sutured to one another. In some embodiments, the third layer may be attached, e.g., sutured to the at least two layers of the ring.

According to some embodiments, the components of a prosthetic mitral valve may be attached or connected to one another via several connection methods. For example, the components of the prosthetic mitral valve may be connected to one another via stitches, stapler pins, glue or any other attachment means.

In some embodiments, the sutures or stitches may be made of non-biodegradable synthetic materials, for example, nylon (ethilon), prolene (polypropylene), Novalfil, polyester, and so on. In some embodiments, the sutures or stitches may be made of non-biodegradable natural materials, such as surgical silk or surgical cotton.

In some embodiments, the stapler pins may be made of biocompatible materials, for example, stainless steel or titanium.

In some embodiments, glue may be made of biocompatible materials such as aldehyde-based glues, fibrin sealarts, collagen-based adhesives, polyethylene glycol polymers (hydrogels), or cyanoacrylates.

According to some embodiments, any of the leaflets, any ring, any cords (and any sub-set of cords) and/or any combination thereof may be customized per patient based upon ultrasound imaging of the patient's native mitral valve and surrounding anatomy. Customized mitral valves may further be produced based on data obtained by other imaging modalities, which provide three-dimensional information, including Echocardiography, cardiac CT and cardiac MRI. As such, mitral valve prostheses of the present disclosure may be selected or designed to match the patient's specific anatomy, thereby to increase the chances of high acceptance of the prostheses by the patient's surrounding tissue, e.g., the heart muscle surrounding the prostheses.

In preparation for implantation to a patient, the heart of the patient is arrested, as is usual for mitral valve surgeries. During implantation, the flexible ring of the prosthesis is affixed by sutures to the native annulus and the papillary caps are sutured to the native papillary muscles. For example, two sutures can be applied at the tip of each of the native papillary muscles, affixing a cap to the muscle. The clinician ensures that the valve will open and close completely by filling the ventricular chamber with a physiological saline under an appropriate pressure and checking the motion and the competence of the replaced valve as it closes due to the exerted pressure. Following implantation, the valve is examined with transesophageal echocardiography (TEE) after the heart is closed and has resumed beating.

If necessary, the subject can be placed on anticoagulation medication following implantation. Given the natural shape and natural materials used to construct mitral valve prostheses of the present invention, low doses of anticoagulation medication or no anticoagulation medication, is expected for most patients.

The currently available biological and mechanical prostheses carry several disadvantages: they contain bulky foreign material, require strong anticoagulation medication, have short useful lives requiring the patient to undergo subsequent surgeries when they must be replaced, and do not assist the heart in recovering efficiently from implantation. The present invention offers several advantages over the biological and mechanical prostheses described above. Having a design that more closely matches the native mitral valve of a patient and being fabricated from natural materials, the mitral valve prostheses described are expected to require less recovery time for the patient, provide a longer useful life, and alleviate or omit the need for anticoagulant medication.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed is:

1. A method for manufacturing a personalized mitral valve prosthesis to precisely fit a specific patient for which the valve prosthesis is made for, wherein said mitral valve prosthesis is designed to resemble a native mitral valve, said method comprising:

measuring parameters of the native mitral valve of the specific patient by using imaging methods, said measuring comprises measuring at least an anterior-posterior (A-P) diameter, an anterolateral-posteromedial (AL-PM) diameter and a width of the annular ring's edge (d);

calculating geometry and dimensions of an annular ring, an anterior leaflet, a posterior leaflet and chords per the specific patient, wherein said calculating comprises calculating an annular ring circumference based on the anterior-posterior diameter and the anterolateral-posteromedial diameter and the width of the annular ring's edge; and cutting and connecting the annular ring, the anterior leaflet, the posterior leaflet and the chords, thereby forming the personalized prosthesis mitral valve.

2. The method of claim 1, wherein said imaging methods comprise: 2D or 3D echocardiography, computed tomography (CT), Cardiac magnetic resonance (CMR) or any combination thereof.

3. The method of claim 1, wherein measuring the parameters of the native mitral valve of the patient further comprises measuring mitral valve related parameters comprising: annulus circumference (AC), annulus area (AA), commissural diameter (C-C), anterior leaflet length (AL), posterior leaflet length (PL), mitral valve shape, and length of chordae tendineae (ACL and PCL).

4. A personalized mitral valve prosthesis comprising
a flexible annular ring dimensioned to match a native mitral annulus of a specific patient,
a flexible anterior leaflet and a flexible posterior leaflet dimensioned to match native mitral leaflets of the specific patient, said leaflets connected to the annular ring and
chords dimensioned to match the native mitral leaflets of the specific patient, said chords—to connect with papillary muscle of the heart, said personalized mitral valve prosthesis is formed by:

measuring parameters of the native mitral valve of the specific patient by using imaging methods, said measuring comprises measuring at least an anterior-posterior (A-P) diameter, an anterolateral-posteromedial (AL-PM) diameter, and a width of the annular ring's edge (d);

calculating geometry and dimensions of the flexible annular ring, the flexible anterior leaflet, the flexible posterior leaflets and chords per the specific patient, wherein said calculating comprising calculating circumference of the flexible annular ring based on the anterior-posterior diameter, the anterolateral-posteromedial diameter and the width of the annular ring's edge; and cutting and connecting the flexible annular ring, the flexible anterior leaflets, the flexible posterior leaflet and chords, thereby forming the personalized prosthesis mitral valve.

5. The personalized mitral valve prosthesis of claim 4, wherein said imaging methods comprise: 2D or 3D echocardiography, computed tomography (CT), Cardiac magnetic resonance (CMR) or any combination thereof.

6. The personalized mitral valve prosthesis of claim 4, wherein measuring the parameters of the native mitral valve of a patient further comprises measuring mitral valve related parameters comprising: annulus circumference (AC), annulus area (AA), commissural diameter (C-C), anterior leaflet length (AL), posterior leaflet length (PL), mitral valve shape, and length of chordae tendineae (ACL and PCL).

7. The personalized mitral valve prosthesis of claim 6, wherein the annular ring circumference (AC) is a function of the anterior-posterior (A-P) diameter and the anterolateral posteromedial (AL-PM) diameter based on equation (iii).

8. The personalized mitral valve prosthesis of claim 7, wherein measuring the anterior-posterior (A-P) diameter and the anterolateral posteromedial (AL-PM) diameter is when the mitral valve closes during left ventricular systole.

9. The personalized mitral valve prosthesis of claim 6, wherein calculating the annular ring circumference (AC) of the prosthesis is based on the annular ring width (d) of preserved native leaflets during clinical surgery.

10. The personalized mitral valve prosthesis of claim 6, wherein calculating the annular ring circumference (AC) of the prosthesis is based on a ratio ($\lambda$) in equation (iii).

11. The personalized mitral valve prosthesis of claim 4, wherein calculating the annular ring circumference (AC) being a combination of anterior leaflet annular ring circumference (AAC) that is a top edge of the anterior leaflet, and posterior leaflet annular ring circumference (PAC) that is a top edge of the posterior leaflet based on equation (iii), further wherein said annular ring is formed into a multi-layered reinforced structure by folding or overlapping the top edge of each of the anterior leaflet and posterior leaflet.

12. The personalized mitral valve prosthesis of claim 11, wherein the top edge of each of the anterior leaflet and the posterior leaflet is straight or curved for properly fitting the personalized mitral valve prosthesis to the natural geometry of left ventricle of the specific patient.

13. The personalized mitral valve prosthesis of claim 11, wherein the reinforced annular ring height is between 1 mm and 4 mm.

14. The personalized mitral valve prosthesis of claim 11, wherein the reinforced annular ring height is between 2 mm and 3 mm.

15. The personalized mitral valve prosthesis of claim 4, wherein connecting comprises stitching the edge of the anterior leaflet with the edge of the posterior leaflet such to create a coaptation between the anterior leaflet and posterior leaflet, wherein the coaptation controls the function and performance of the personalized mitral valve prosthesis by controlling the size of valve orifice and thus affect the trans-mitral pressure gradient.

16. The personalized mitral valve prosthesis of claim 4, wherein connecting comprises stitching the two leaflets together thereby forming two commissures, wherein the two commissures incline inward in a cone angle ($\delta_1$) to create a slight cone shape to the body of the personalized mitral valve prosthesis to properly fit in the native left ventricle per shape and contour of the specific patient.

17. The personalized mitral valve prosthesis of claim 16, wherein the cone angle ($\delta_1$) is determined by an inclined angle ($\delta_0$) of each commissure edge of the two leaflets based on equation (x).

18. The personalized mitral valve prosthesis of claim 4, wherein connecting comprises connecting the flexible anterior leaflet to the flexible posterior leaflet by connecting anterolateral side to anterolateral side and connecting posteromedial side to posteromedial side.

19. The personalized mitral valve prosthesis of claim 18, wherein connecting the flexible anterior leaflet to the flexible posterior leaflet is by stitching.

20. The personalized mitral valve prosthesis of claim 4, wherein measuring comprises measuring: size and shape of a native annular ring of the specific patient, commissure height (CH), inclined angel ($\delta_0$), anterior leaflet length (AL) and posterior leaflet length (PL), and coaptation height (Coapt H) for calculating length of each leaflet edge based on equation (xi).

21. The personalized mitral valve prosthesis of claim 20, wherein calculating comprises calculating the anterior leaflet length (AL) and posterior leaflet length (PL) based on: (a) an anterior-posterior (A-P) diameter that is a theoretical minimum distance for coaptation, (b) a ratio (r) between AL to PL, (c) coaptation depth (Cd), (d) the coaptation height (Coapt H) and (e) chord length (Lc) based on equations (viii) and (ix), respectively.

22. The personalized mitral valve prosthesis of claim 4, wherein the annular ring is asymmetrical and further wherein said annular ring is formed from a combination of an anterior leaflet annulus and a posterior leaflet annulus, wherein anterior leaflet annular circumference (AAC) is smaller than posterior leaflet annular circumference (PAC), and the ratio (R) between AAC/PAC is between 49/51 and 30/70.

23. The personalized mitral valve prosthesis of claim 22, wherein ratio (R) between AAC/PAC is between 35/65 and 42/58.

24. The personalized mitral valve prosthesis of claim 22, wherein ratio (R) between AAC/PAC is 40/60.

25. The personalized mitral valve prosthesis of claim 22, wherein ratio (R) between AAC/PAC is between anterior leaflet length (AL) and posterior leaflet length (PL) and is crucial to ensure the prosthesis valve opens and closes properly.

26. The personalized mitral valve prosthesis of claim 4, wherein connecting comprises connecting the two flexible leaflets together to form a body of the personalized mitral valve prosthesis.

27. The personalized mitral valve prosthesis of claim 4, wherein each of the flexible anterior leaflet and each of the flexible posterior leaflet comprises two sets of chords: anterolateral chords and posteromedial chords, wherein each of the anterolateral chords and posteromedial chords comprises three sub-chords, wherein the cords are uniformly distributed along at least ⅜ of each edge from each side.

28. The personalized mitral valve prosthesis of claim 27, wherein calculating comprises calculating length of each chord to ensure the personalized mitral valve prosthesis opens and closes properly, wherein calculating length of each chord is based on several parameters comprising: leaflet length, coaptation height, and coaptation depth.

29. The personalized mitral valve prosthesis of claim 4, wherein measuring comprises measuring distance from a papillary muscle apex to a coaptation edge to denote a prosthesis chord length, further comprising on-site measuring and adjusting of a pledget like chord cap into which the chords are integrated and merged at an end of each set of chords.

30. The personalized mitral valve prosthesis of claim 4, further comprising implementing calculated geometry and dimensions of annular ring, anterior leaflet, posterior leaflet and chords per the specific patient as inputs for an engineering drawing software or drawing tools.

31. The personalized mitral valve prosthesis of claim 30, wherein said engineering drawing software or drawing tools output a template for manually cutting the leaflets of the valve prosthesis.

32. The personalized mitral valve prosthesis of claim 30, wherein said engineering drawing software or drawing tools output a template for machine cutting the leaflets.

33. The personalized mitral valve prosthesis of claim 4, further comprising packing, labelling and sterilizing the personalized mitral valve prosthesis before release for usage.

34. The personalized mitral valve prosthesis of claim 4, further comprising assembling the personalized mitral valve prosthesis onto a valve holder before packaging.

35. The personalized mitral valve prosthesis of claim 4, further comprising implanting the personalized mitral valve prosthesis into the specific patient.

36. The personalized mitral valve prosthesis of claim 4, wherein the mitral valve prosthesis is a biomimicry mitral valve prosthesis.

* * * * *